United States Patent [19]

Heitsch et al.

[11] Patent Number: 5,635,525

[45] Date of Patent: Jun. 3, 1997

[54] BENZIMIDAZOLE DERIVATIVES AS ANGIOTENSIN II RECEPTOR ANTAGONISTS, PHARMACTICALS, AND TREATMENT OF HYPERTENSION THEREWITH

[75] Inventors: Holger Heitsch, Hofheim am Taunus; Adalbert Wagner, Hattersheim am Main; Heinz-Werner Kleemann, Bad Homburg; Hermann Gerhards, Hofheim am Taunus; Bernward Schölkens, Kelkheim, all of Germany

[73] Assignee: Hoechst Aktiengesellschaft, Frankfurt am Main, Germany

[21] Appl. No.: 463,299

[22] Filed: Jun. 5, 1995

Related U.S. Application Data

[62] Division of Ser. No. 165,655, Dec. 13, 1993, Pat. No. 5,444,068, which is a division of Ser. No. 942,769, Sep. 10, 1992, abandoned.

[30] Foreign Application Priority Data

Sep. 14, 1991 [DE] Germany ............. 41 30 659.7
Sep. 20, 1991 [DE] Germany ............. 41 31 325.9

[51] Int. Cl.⁶ ............. A61K 31/495; A61K 31/435; C07D 471/04; C07D 473/00
[52] U.S. Cl. ............. 514/394; 514/395; 514/397; 548/304.4; 548/306.4; 548/309.4; 548/309.7
[58] Field of Search ............. 548/309.7, 304.4; 514/397, 394, 395

[56] References Cited

U.S. PATENT DOCUMENTS

| | | | |
|---|---|---|---|
| 4,728,741 | 3/1988 | Kaiser et al. | 548/309.7 X |
| 5,298,518 | 3/1994 | Miyake et al. | 514/381 |
| 5,314,880 | 5/1994 | Whittaker et al. | 514/80 |
| 5,376,666 | 12/1994 | Duncia | 514/303 |
| 5,395,840 | 3/1995 | Muller et al. | 514/300 |
| 5,395,844 | 3/1995 | Duncia et al. | 514/333 |

FOREIGN PATENT DOCUMENTS

| | | | |
|---|---|---|---|
| 392317 | 10/1990 | European Pat. Off. | 548/304.4 |
| 399731 | 11/1990 | European Pat. Off. | 548/304.4 |
| 399732 | 11/1990 | European Pat. Off. | 548/304.4 |
| 400974 | 12/1990 | European Pat. Off. | 548/304.4 |
| 400835 | 12/1990 | European Pat. Off. | 548/304.4 |

*Primary Examiner*—Floyd D. Higel
*Attorney, Agent, or Firm*—Finnegan, Henderson, Farabow, Garrett & Dunner, L.L.P.

[57] ABSTRACT

A compound of the formula

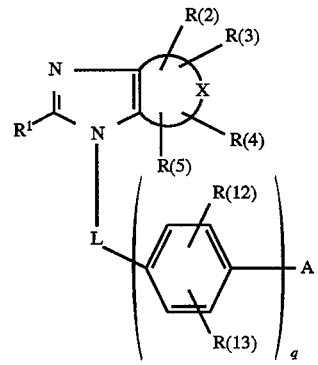

in which the symbols have the following meaning:
X is a monocyclic radical having 3, 4 or 5 ring atoms,
$R^1$, $R^2$, $R^3$, $R^4$, $R^{12}$ and $R^{13}$ are, for example, an alkyl radical,
q is zero or 1,
L is, for example, a methylene group and
A is the radical, for example, of a heterocycle are highly active as antagonists of angiotensin II receptors.

They can be used as pharmaceuticals or diagnostics.

10 Claims, No Drawings

BENZIMIDAZOLE DERIVATIVES AS ANGIOTENSIN II RECEPTOR ANTAGONISTS, PHARMACTICALS, AND TREATMENT OF HYPERTENSION THEREWITH

This application is a division of U.S. patent application Ser. No. 08/165,655 filed Dec. 13, 1993 which issued on Aug. 22, 1995, as U.S. Pat. No. 5,444,068, which is a division patent application Ser. No. 07/942,769 filed Sep. 10, 1992, now abandoned.

EP-A 399,731, EP-A 399,732, EP-A 400,835 and EP-A 434,038 disclose imidazo-fused aromatic compounds as antagonists of angiotensin II receptors. However, none of these literature sources describe compounds which simultaneously have a cyclically substituted phenyl ring as a substituent on the nitrogen of the imidazole ring and a heterocycle fused to the imidazole ring; just as few compounds are disclosed or suggested which bear a homo-aromatic compound fused to the imidazole and at the same time a biphenyl group on the nitrogen atom of the imidazole; likewise, no compounds are disclosed which bear a sulfonylurea or sulfonylurethane radical on the biphenylyl group.

Imidazole derivatives have now been found which are surprisingly highly active antagonists of angiotensin II receptors both in vitro and in vivo.

The invention relates to compounds of the formula

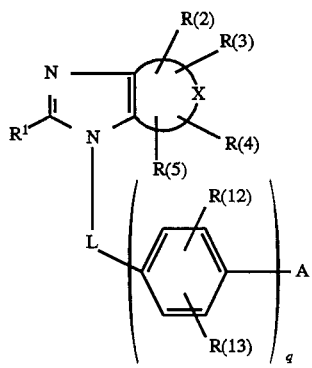

(I)

in which the symbols have the following meanings

X is a monocyclic radical having 3, 4 or 5 ring atoms or a bicyclic radical having 8–10 ring atoms, which radical can be completely or partially hydrogenated and in which one or more CH or $CH_2$ groups can be replaced by N, NH or O;

R(1) is

1. $(C_1-C_{10})$-alkyl,
2. $(C_3-C_{10})$-alkenyl,
3. $(C_3-C_{10})$-alkynyl,
4. OR(6),
5. $(C_3-C_8)$-cycloalkyl,
6. $(C_4-C_{10})$-cycloalkylalkyl,
7. $(C_5-C_{10})$-cycloalkylalkenyl,
8. $(C_5-C_{10})$-cycloalkylalkynyl,
9. $(CH_2)_m$—B—$(CH_2)_m$—R(7),
10. benzyl,
11. a radical as defined in 1., 2., 3. or 9., which is monosubstituted by $CO_2R(6)$,
12. a radical as defined in 1., 2., 3. or 9., in which 1 to all of the hydrogen atoms are substituted by fluorine, or
13. the radical defined in 10. which is substituted on the phenyl by 1 or 2 identical or different radicals from the series comprising halogen, $(C_1-C_4)$-alkoxy and nitro;

R(2), R(3), (R4) and R(5) are identical or different and are 1. hydrogen, halogen, hydroxyl, cyano, nitro, sulfo, formyl, benzoyl, $(C_1-C_8)$-acyl, $(C_1-C_8)$-acyloxy, mercapto, carboxyl, $(C_1-C_4)$-alkoxy-carbonyl,
2. a linear or branched, optionally substituted alkyl, alkenyl, alkoxy or allylthio radical containing up to 6 carbon atoms,
3. an aryl, arylalkyl or arylalkenyl radical in which the alkyl and alkenyl substituent in unbranched or branched form has up to 6 carbon atoms and the aryl substituent is a monacyclic radical having 5 or 6 ring atoms or condensed rings having 8 to 14 ring atoms, in which one or more hetero atoms such as O, N or S are contained and which are optionally substituted,
4. a radical

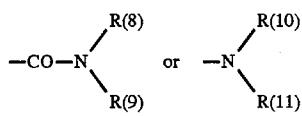

R(6) is 1. hydrogen,
2. $(C_1-C_8)$-alkyl,
3. $(C_3-C_8)$-cycloalkyl,
4. phenyl,
5. benzyl or the radical defined in 2., in which 1 to all of the hydrogen atoms are substituted by fluorine;

R(7) is 1. hydrogen,
2. $(C_1-C_6)$-alkyl,
3. $(C_3-C_8)$-cycloalkyl
4. $(C_2-C_4)$-alkenyl or
5. $(C_2-C_4)$-alkynyl;

R(8) and R(9) or R(10) and R(11) are either identical or different and are 1. hydrogen,
2. $(C_1-C_6)$-alkyl or $(C_1-C_6)$-alkenyl, unsubstituted or substituted by halogen, hydroxyl or $(C_1-C_6)$-alkoxy,
3. aryl or $(C_1-C_6)$-alkylaryl, in which the aryl radical is monocyclic having 5 or 6 ring atoms or bicyclic having 8–10 ring atoms, optionally contains one or more hereto atoms such as O, N and S and is substituted by 1 or 2 identical or different radicals from the series comprising halogen, hydroxyl, nitro, $(C_1-C_6)$-alkyl, $(C_1-C_6)$-alkenyl, $(C_1-C_4)$-alkanoyl, $(C_1-C_4)$-alkanoyloxy and $CO_2R^6$;

or

R(8) and R(9) or R(10) and R(11), together with the nitrogen atom bearing them, form a 4- to 8-membered ring which is saturated or unsaturated, can contain a further hetero atom selected from the group comprising N, O and S and is unsubstituted or substituted by halogen, hydroxyl, $(C_1-C_4)$-alkyl, $(C_1-C_4)$-alkenyl, $(C_1-C_4)$-alkyloxy and $CO_2R(6)$, or R(10) and R(11) are either identical or different and are an acyl radical of up to 6 carbon atoms or a $(C_1-C_6)$-alkyl or $(C_6-C_{12})$-aryl radical which is optionally substituted by halogen or $(C_1-C_6)$-alkyl radicals;

L is $(C_1-C_3)$-alkanediyl;

R(12) and R(13) are identical or different and are 1. hydrogen,
2. halogen,
3. nitro,
4. $(C_1-C_4)$-alkyl or
5. $(C_1-C_2)$-alkoxy;

q is zero or 1;

A is either 1. the radical of a heterocycle having 5–10 ring atoms, which can be mono- or bicyclic, and of which up to 9 ring atoms are carbon atoms, which radical is unsubstituted or substituted by up to 6, preferably up to 3, identical or different radicals R(14) and R(15), or
2. a biphenyl radical which is unsubstituted or substituted by up to 4, preferably up to 2, identical or different radicals R(14) and R(15), where A, however, must be substituted by at least one radical defined in R(15) 18., 19., 28., 40. or 42. and q=zero, R(14) is 1. halogen,
2. oxo,
3. nitroso,
4. nitro,
5. amino,
6. cyano,
7. hydroxyl,
8. $(C_1-C_6)$-alkyl,
9. $(C_1-C_4)$-alkanoyl,
10. $(C_1-C_4)$-alkanoyloxy,
11. $CO_2R(6)$,
12. methanesulfonylamino,
13. trifluoromethanesulfonylamino,
14. —CO—NH—OR(16),
15. —$SO_2$—NR(17)R(18),
16. —$CH_2$—OR(18),
17. $(C_1-C_4)$-heteroaryl-$(CH_2)_q$-, preferably 1-tetrazolyl,
18. $(C_7-C_{13})$-aroyl, 19. 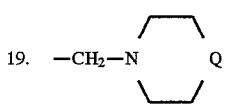

20. 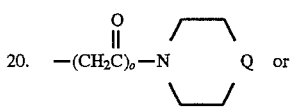 or

21. $(C_6-C_{12})$-aryl;

R(15) is 1. hydrogen,
2. $(C_1-C_6)$-alkyl,
3. $(C_3-C_8)$-cycloalkyl,
4. $(C_6-C_{12})$-aryl,
5. $(C_1-C_4)$-aroyl,
6. $(C_1-C_4)$-alkoxy,
7. $(C_1-C_4)$-alkanoyloxy,
8. $(C_1-C_9)$-heteroaryl,
9. $CO_2R(6)$,
10. halogen,
11. cyano,
12. nitro,
13. NR(17)R(18),
14. hydroxyl,
15. —CO—NH—CHR(19)—$CO_2R(6)$,
16. sulfo,
17. —$SO_3R(6)$,
18. —$SO_2$—NR(18)—CO—NR(17)R(16), —$SO_2$—NR(18)—CO—O—R(17), —$SO_2N(CO$—O—$R(17))_2$ or —$SO_2$—NR(18)—CS—NR(17)R(16),
19. —NR(18)—CO—NR(17)—$SO_2$—$CH_2$—R(18),
20. —$C(CF_3)_2OH$,
21. phosphonooxy,
22. —$PO_3H_2$,
23. —NH—$PO(OH)_2$,
24. —$S(O)_rR(17)$,
25. —CO—R(20),
26. —CO—NR(17)R(16), 27. 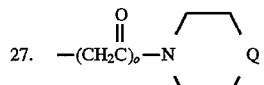

28. 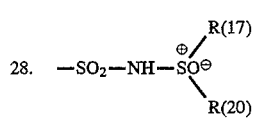

29. 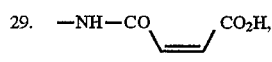

30. 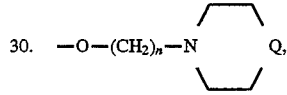

31. 5-tetrazolyl-NH—CO—,
32. —CO—NH—NH—$SO_2$—$CF_3$,

33. 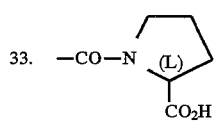

34. 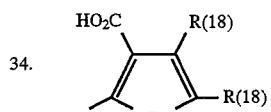

35. 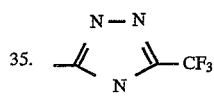

36. 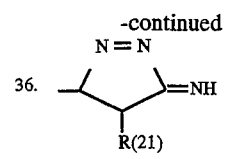

37. 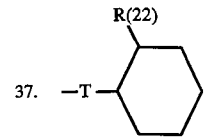

38. 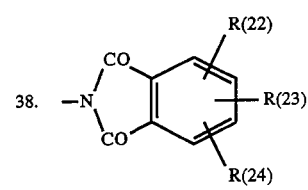

39. —CO—NH—SO$_2$—R(6),

40. —SO$_2$—NH—CO—R(17), 41. the radical defined in 4., substituted by 1 or 2 identical or different radicals from the series comprising halogen, cyano, nitro, NR(17)R(18) and hydroxyl, 42. R(15) together with R(14) is —CO—NH—SO$_2$—;

R(16) and R(17) are identical or different and are 1. hydrogen,
2. (C$_1$–C$_6$)-alkyl,
3. (C$_3$–C$_8$)-cycloalkyl,
4. (C$_6$–C$_{12}$)-aryl, preferably phenyl,
5. (C$_6$–C$_{10}$)-aryl-(C$_1$–C$_4$)-alkyl,
6. (C$_1$–C$_9$)-heteroaryl which can be partially or completely hydrogenated, preferably 2-pyrimidinyl, 1-piperidinyl, or quinuclidinyl,
7. (C$_3$–C$_6$)-alkenoyl,
8. a radical as defined in 4., 5., 6., 9., 14., 15., 16., 18., 19. or 20., substituted by 1 or 2 identical or different radicals from the series comprising hydroxyl, methoxy, nitro, cyano, CO$_2$R(6), trifluoromethyl, —NR(25)R(26) and

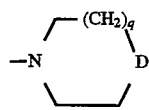

9. (C$_1$–C$_9$)-heteroaryl-(C$_1$–C$_3$)-alkyl, where the heteroaryl moiety can be partially or completely hydrogenated,
10. the radical defined in 2., in which 1 to all of the hydrogen atoms are substituted by fluorine,
11. (C$_2$–C$_6$)-alkenyl,
12. (C$_3$–C$_8$)-cycloalkenyl,
13. (C$_3$–C$_8$)-cycloalkenyl-(C$_1$–C$_3$)-alkyl,
14. (C$_3$–C$_8$)-cycloalkyl-(C$_1$–C$_4$)-alkyl,
15. (C$_6$–C$_{10}$)-aryl-(C$_3$–C$_6$)-alkenyl,
16. (C$_1$–C$_9$)-hetaryl-(C$_3$–C$_6$)-alkenyl,
17. (C$_3$–C$_6$)-alkynyl,
18. (C$_6$–C$_{10}$)-aryl-(C$_3$–C$_6$)-alkynyl,
19. (C$_1$–C$_9$)-hetaryl-(C$_3$–C$_6$)-alkynyl, 20. a radical of the formula

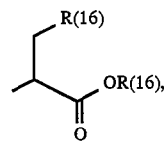

where R(16) cannot have the meaning of 20. Stereocenters can be present either in the R- or in the S-configuration.

21. R(16)R(17), together with the nitrogen atom bearing them, form a hetaryl which can also be partially or completely hydrogenated;

R(18) is 1. hydrogen,
2. (C$_1$–C$_6$)-alkyl,
3. (C$_3$–C$_8$)-cycloalkyl,
4. (C$_6$–C$_{12}$)-aryl-(C$_1$–C$_6$)-alkyl, preferably benzyl,
5. phenyl or
6. (C$_1$–C$_9$)-heteroaryl;

R(19) is 1. hydrogen,
2. (C$_1$–C$_6$)-alkyl,
3. (C$_3$–C$_8$)-cycloalkyl,
4. phenyl or
5. benzyl;

R(20) is 1. hydrogen,
2. (C$_1$–C$_6$)-alkyl,
3. (C$_3$–C$_8$)-cycloalkyl,
4. phenyl-(CH$_2$)$_q$-,
5. OR(19),
6. NR(25)R(26) or 7. 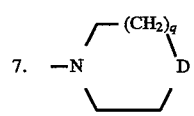

R(21) is cyano, nitro or CO$_2$R(18);
R(22) is CO$_2$R(6) or CH$_2$CO$_2$R(6);
R(23) is hydrogen, halogen, (C$_1$–C$_4$)-alkyl or (C$_1$–C$_4$)-alkoxy
R(24) is hydrogen, (C$_1$–C$_4$)-alkyl or phenyl;
R(25) and R(26) are identical or different and are 1. hydrogen,
2. (C$_1$–C$_4$)-alkyl,
3. phenyl,
4. benzyl or
5. α-methylbenzyl;

D is NR(23), O or CH$_2$;
B is O, NR(18) or S;
T is 1. a single bond,
2. —CO—,
3. —CH$_2$—,
4. —O—, 5. —S—,
6. —NR(28)—,
7. —CO—NR(28)—,
8. —NR(28)—CO—,
9. —O—CH$_2$—,
10. —CH$_2$—O—,
11. —S—CH$_2$—,
12. —CH$_2$—S—,
13. —NH—CR(27)R(29)—,
14. —NR(28)—SO$_2$—,
15. —SO$_2$—NR(28)—,
16. —CR(27)R(29)—NH—,
17. —CH=CH—,
18. —CF=CF—,
19. —CH=CF—,
20. —CF=CH—,
21. —CH$_2$—CH$_2$—,
22. —CF$_2$—CF$_2$—,
23. —CH(OR)(6))—,
24. —CH(OCOR(19))—, 25. 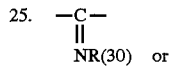
$$\begin{array}{c} -C- \\ \parallel \\ NR(30) \end{array} \text{ or }$$

26. 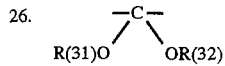
$$\begin{array}{c} -C- \\ / \phantom{xx} \backslash \\ R(31)O \phantom{xx} OR(32) \end{array}$$

R(27) and R(29) are identical or different and are hydrogen, (C$_1$–C$_5$)-alkyl, phenyl, allyl or benzyl;
R(28) is hydrogen, (C$_1$–C$_6$)-alkyl, benzyl or allyl;
R(30) is 1. NR(27)R(28),
2. ureido,
3. thioureido,
4. toluene-4-sulfonyl or
5. benzenesulfonylamino;

R(31) and R(32) are identical or different and are (C$_1$–C$_4$)-alkyl or together are —(CH$_2$)$_q$—;
Q is CH$_2$, NH, O or S;
n is an integer from 1 to 5;
m is an integer from 0 to 3;
o is an integer from 1 to 10;
r is zero, 1 or 2
and their physiologically tolerable salts.

Alkyl, alkenyl and alkynyl can be straight-chain or branched. The same applies to radicals derived from these, such as alkanoyl or alkoxy.

Cycloalkyl is also understood as meaning alkyl-substituted rings.

(C$_6$–C$_{12}$)-aryl is, for example, phenyl, naphthyl or biphenylyl, preferably phenyl. The same applies to radicals derived from these, such as aroyl or aralkyl.

(C$_1$–C$_9$)-heteroaryl is in particular understood as meaning radicals which are derived from phenyl or naphthyl, in which one or more CH groups are replaced by N and/or in which at least two adjacent CH groups are replaced (with the formation of a 5-membered aromatic ring) by S, NH or O. Furthermore, one or both atoms of the condensation site of bicyclic radicals (such as in indolizinyl) can also be a nitrogen atom.

These radicals are, for example, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyradiazinyl, indolyl, indazolyl, quinolyl, isoquinolyl, phthalazinyl, quinoxalinyl, quinazolinyl, cinnolinyl.

The fused heterobicycle AH, from which the radical A is derived, is in particular understood as meaning a bicyclic ring system having 8 to 10 ring atoms of which up to 9 ring atoms are carbon atoms, in which two adjacent atoms are together constituents of both rings. One or both of these rings are formally derived from benzene in which one or more CH groups are replaced by N, O$^+$ and S$^+$ and/or in which two adjacent CH groups are replaced (with the formation of a 5-membered aromatic ring) by S, NH or O.

A, for example, is a radical of benzothiophene, benzofuran, indole, isoindole, indazole, benzimidazole, quinoline, isoquinoline, phthalazine, quinoxaline, quinazoline, cinnoline, benzothiazole, benzothiazole-1,1-dioxide, coumarin, chroman, benzoxazole, benzisothiazole, benzodiazine, benzotriazole, benzotriazine, benzoxazine, imidazopyridine, imidazopyrimidine, imidazopyrazine, imidazopyridazine, imidazothiazole, pyrazolopyridine, thienopyridine and pyrrolopyrimidine. Said heterobicycle AH can also be partially or completely hydrogenated. Preferably, however, one ring of AH remains aromatic, a benzo-fused heterobicycle AH being particularly preferred.

In the case of S-containing and/or partially saturated radicals, the bicycle can also be, for example, oxo-substituted as is the case in the radical of benzo-1,2,3-triazinone.

The linkage of A takes place by the isocyclic or by the heterocyclic moiety, in the case where q=zero via an alkanediyl bridge L and in the case where q=1 via a single bond to give the

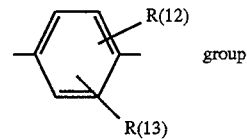 group

An iso- or heterocycle XH$_2$, from which the mono- or bicyclic radical X is derived, is understood as meaning, for example, a radical of cyclopentane, cyclohexane, cycloheptane, cyclopentene, cyclohexene, cycloheptene, benzene, naphthalene, furan, thiophene, pyrrole, pyridine, pyridazine, pyrimidine, piperidine, piperazine, morpholine, indole, indazole, oxazole, isoxazole, quinoline, isoquinoline, benzothiophene, benzofuran, benzothiazole, benzoxazole, imidazopyridine, imidazopyrimidine and furopyridine. Halogen is fluorine, chlorine, bromine or iodine.

Physiologically tolerable salts of compounds of the formula I are understood as meaning both their organic and inorganic salts, such as are described in Remington's Pharmaceutical Sciences, 17th Edition, page 1418 (1985). On the basis of physical and chemical stability and solubility, preferred acidic groups are, inter alia, sodium, potassium, calcium and ammonium salts, and basic groups are, inter alia, salts with hydrochloric acid, sulfuric acid, phosphoric acid, carboxylic acids or sulfonic acids, such as acetic acid, citric acid, benzoic acid, maleic acid, fumaric acid, tartaric acid and p-toluenesulfonic acid.

Preferred compounds are those of the formula II:

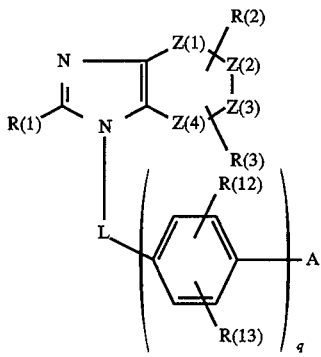

in which the symbols have the following meaning:
Z(1), Z(2), Z(3) and Z(4) are:

1. —CH$_2$—,
2. —CH=,
3. a radical defined in 2., where 1 or 2 methine groups are replaced by nitrogen; preferably Z(4)=N, R(1) is 1. (C$_1$–C$_{10}$)-alkyl,
2. (C$_3$–C$_{10}$)-alkenyl,
3. (C$_3$–C$_{10}$)-alkynyl,
4. (C$_3$–C$_8$)-cycloalkyl,
5. benzyl or
6. benzyl which is substituted as described above;

R(2) and R(3) are identical or different and are:

1. hydrogen,
2. hydroxyl,
3. halogen,
4. a linear or branched (C$_1$–C$_6$)-alkyl radical, unsubstituted or substituted by one or more identical or different substituents from the series comprising halogen, hydroxyl, (C$_1$–C$_4$)-alkoxy, (C$_1$–C$_4$)-alkylthio and mercapto,
5. —CO$_2$R(6);

T is a single bond, —O—, —CO—, —NHCO— or —OCH$_2$— and the other radicals and variables are as defined above.

Particularly preferred compounds of the formula II are those in which
R(1) is (C$_1$–C$_7$)-alkyl, (C$_3$–C$_7$)-alkenyl or (C$_3$–C$_7$)-alkynyl;
R(6) is hydrogen or (C$_1$–C$_4$)-alkyl;
R(12) and R(13) are identical or different and are hydrogen or (C$_1$–C$_4$)-alkyl;
R(14) is 1. (C$_1$–C$_4$)-alkyl,
2. (C$_1$–C$_4$)-alkoxy,
3. cyano,
4. amino,
5. nitro,
6. fluorine, chlorine or bromine,
7. (C$_1$–C$_4$)-heteroaryl-CH$_2$,
8. (C$_1$–C$_4$)-alkanoyloxy,
9. (C$_1$–C$_4$)-alkanoyl,
10. benzoyl or
11. tetrazolyl;

R(15) is 1. (C$_1$–C$_4$)-alkyl,
2. (C$_6$–C$_{12}$)-aryl,
3. (C$_{1-3}$)-alkanoyloxy,
4. (C$_1$–C$_4$)-alkoxy,
5. (C$_1$–C$_9$)-heteroaryl, preferably 5-tetrazolyl,
6. cyano,
7. nitro,
8. hydroxyl,
9. SO$_3$R(6),
10. chlorine, bromine,
11. CO$_2$R(6),
12. CO—NH—R(19),
13. CO—R(20),
14. SO$_2$—NR(18)—CO—NR(17)R(16),
15. SO$_2$NR(18)—CO—O—R(17) or SO$_2$N(CO—OR(17))$_2$,
16. CO—CHR(19)—CO$_2$H,
17. (C$_1$–C$_4$)-alkyl—CO$_2$H,
18. NH—CO—NH—SO$_2$—CH$_2$—R(19), 20. 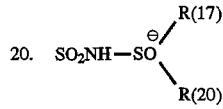

21. 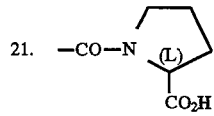

22. 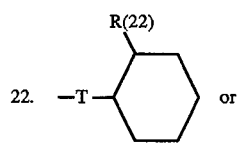 or

23. R(14) with R(15) together are —CO—NH—SO$_2$;
L is —CH$_2$—;
R(18) is hydrogen;
R(25) and R(26), independently of one another, are hydrogen or (C$_1$–C$_4$)-alkyl, and their physiologically tolerable salts.

The invention also relates to a process for the preparation of compounds of the formula I, which comprises alkylating compounds of the formula III

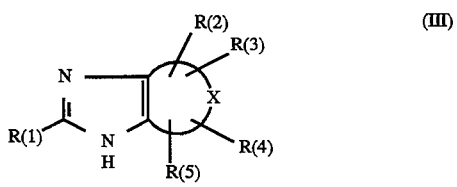

in which R(1), R(2), R(3), R(4), R(5) and X are as defined above, with compounds of the formula IV

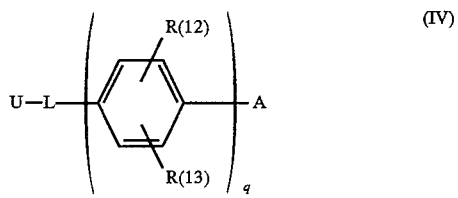

in which L, q, R(12), R(13) and A are as defined above and U is a leaving group, optionally removing temporarily introduced protective groups again and optionally converting the compounds of the formula I obtained into their physiologically tolerable salts.

Suitable leaving groups U are preferably nucleofugic groups (cf. Angew. Chem. 72 (1960)) such as halogen, o-toluenesulfonate, mesylate or triflate.

Processes for the preparation of the precursors of the formula III are disclosed, inter alia, in U.S. Pat. No. 4,880,804, DE 3,911,603, EP-A-399,731, EP-A-399,732, EP-A-400,835, EP-A-400,974, EP-A-415,886, EP-A-420,237, EP-A-425,921 and EP-A-434,038.

For the alkylation of the compounds of the formula III, for example, appropriate benzyl halides, tosylates, mesylates or triflates or appropriate alkyl halides, tosylates, mesylates or triflates are suitable.

These compounds are prepared in a manner known per se, for example halogenation of the corresponding methyl precursors. For this purpose, N-bromosuccinimide is preferably employed, see, for example, J. Org. Chem. 44, 4733 (1979) and Helv. Chim. Acta 62, 2661 (1979).

The synthesis of the benzimidazole, benzothiophene, imidazopyridine and imidazopyrimidine derivatives having a $CH_3$ group on the ring is carried out, inter alia, according to R. P. Dickson et al. in J. Med. Chem. 29, 1637 (1986), E. Abignente et al. in J. Heterocyclic Chem. 26, 1875 (1989), A. Koubsack et al. in J. Org. Chem. 41, 3399 (1976) and according to F. Santer et al. in Mh. Chem. 99, 715 (1968).

The biphenyl derivatives can be synthesized, for example, starting from arylboronic acid derivatives by coupling with substituted aryl halides using transition metal catalysts, in particular palladium. Appropriate reactions are described by R. B. Miller et al. (Organometallics 1984, 3, 1261) or by A. Zuzuki etal. (Synthetic Commun. 11 (7), 513 (1981)).

The sulfonylurethane derivatives of the formula (I) can be obtained from appropriate sulfonamides of the formula (I) by reaction with chlorocarbonic acid esters, or by reacting with dimethyl dicarbonate and bases such as, for example, potassium carbonate in inert solvents at temperatures up to the boiling point of the appropriate solvent.

The sulfonylurea derivatives of the formula (I) can be prepared, as desired, either from the appropriate sulfonamides of the formula (I) by reaction with isocyanates or with 2,2,2-trichloroacetamide derivatives of a suitable amine in inert, high-boiling solvents such as, for example, DMSO or from sulfonyl urethanes of the formula (I) by action of the appropriate amine in an inert, high-boiling solvent such as, for example, toluene at temperatures up to the boiling point of the respective solvent.

If necessary, the sulfonamide radical can be prepared starting from an amino group by means of Meerwein rearrangement. For this purpose, the hydrochloride of the amine is first diazotized and then reacted with sulfur dioxide in glacial acetic acid in the presence of a copper catalyst. Subsequent action of ammonia leads to the sulfonamido group.

Alkylation is carried out in an analogous manner by processes known in principle.

The imidazo-fused derivatives of the formula III are metalated, for example, in the presence of a base. Preferred bases are metal hydrides of the formula MH such as lithium hydride, sodium hydride or potassium hydride in, for example, DMF or DMSO as the solvent or metal alkoxides of the formula MOR, where R is methyl, ethyl or t-butyl, and the reaction is carried out in the appropriate alcohol, DMF or DMSO. The salts of the imidazo derivatives thus formed are dissolved in an aprotic solvent such as DMF or DMSO and treated with a suitable amount of alkylating reagent.

An alternative possibility for deprotonation of the imidazole derivatives is, for example, reaction with potassium carbonate in DMF or DMSO.

The reactions are carried out for about 1 to 10 hours at temperatures below room temperature up to the boiling point of the reaction mixture, preferably between +20° C. and the boiling point of the reaction mixture.

The compounds of the formula I according to the invention have antagonistic action on angiotensin II receptors and can therefore be used for the treatment of angiotensin II-dependent hypertension. Possibilities of use furthermore exist in cardiac insufficiency, cardioprotection, myocardial infarct, cardiac hypertrophy, arteriosclerosis, nephropathy, kidney failure and cardiovascular diseases of the brain such as transitory ischemic attacks and cerebral apoplexy.

Renin is a proteolytic enzyme of the aspartylprotease class, which is secreted into the blood circulation from the juxtaglomerular cells of the kidney as a result of various stimuli (volume depletion, sodium deficiency, α-receptor stimulation). There it cleaves the decapeptide angiotensin I from the angiotensinogen secreted by the liver. This is converted into angiotensin II by the "angiotensin converting enzyme" (ACE). Angiotensin II plays an essential role in blood pressure regulation, as it directly increases the blood pressure by vascular contraction. Additionally, It stimulates the secretion of aldosterone from the adrenal gland and in this manner increases the extracellular fluid volume by means of the inhibition of sodium excretion, which in turn contributes to an increase in blood pressure.

Post-receptor effects are, inter alia, stimulation of phosphoinositol conversion ($Ca^{2+}$ release), activation of protein kinase C and facilitation of AMP-dependent hormone receptors.

The affinity of the compounds of the formula I for the angiotensin II receptor can be determined by measurement of $^{125}$I-angiotensin II or $^3$H-angiotensin II displacement from receptors on Zona glomerulosa membranes of bovine adrenal glands. To do this, the prepared membranes are suspended in buffer at pH 7.4. In order to prevent the degradation of the radioligand during incubation, aprotinin, a peptidase inhibitor, is added. About 14000 cpm of a tracer having a specific activity of 74 TBq/mmol (commercially available from Amersham Buchler) and an amount of receptor protein which binds 50% of the tracer are additionally used. The reaction is started by addition of 50 μl of membrane suspension to a mixture of 100 μl of buffer+aprotinin, 50 μl of buffer with or without angiotensin II or receptor antagonist and 50 μl of tracer. After an incubation period of 60 minutes at 25° C., bound and free radioligand are separated by a filtration assay using Whatmann® GFIC filters on a Skatron® cell collector.

Non-specific banding is prevented by treatment of the filter with 0.3% polyethyleneimine pH=10 (Sigma, No. 3143). By measurement of the radioactivity in a gamma scintillation counter, the strength of the displacement of the radioligand of the receptor is determined. The $IC_{50}$ values, which denote the concentration of the inhibitor necessary to displace 50% of the ligand, are determined according to Chem. et al. J. Theor. Biol. 59,253 (1970). For the compounds of the formula (I) they are in the range from $1 \times 10^{-4}$–$1 \times 10^{-9}$M.

Alternatively, the affinity of the compounds of the formula I for the angiotensin II receptor can be determined by measurement of the $^{125}$I angiotensin II or $^3$H angiotensin II displacement of receptor preparations from various organs (liver, lung, adrenal gland, brain etc.).

For this purpose, the prepared membranes are suspended in an incubation buffer (20 mM tris, pH 7.4, containing 135 mM NaCl, 10 mM KCl, 10 mM $MgCl_2$, 5 mM glucose, 0.2% bovine serum albumin and the protease inhibitors PMSF 0.3 mM and bacitracin 0.1 mM) and incubated at 25° C. for 90 min together with the radioactively labeled angiotensin II and various concentrations of the compounds to be tested. Bound and free radioligand are then separated by filtration through micro glass fiber filters (GF51, Schleicher & Sch üll) on a cell collector (SKATRON).

By measurement of the receptor-bound radioactivity on the filters by means of a beta spectrometer or gamma spectrometer, the degree of displacement of the radioligand from the receptor by the test compounds is determined. The potency of the displacement of the radioligand from the receptor by the test compounds is given by the $IC_{50}$, i.e. the concentration of the inhibitor which displaces 50% of the bound radioligand from the receptor. The calculation of the $IC_{50}$ values is carried out by means of PC software (LIGAND, G. A. McPherson 1985, Elsevier-BIOSOFT, 68 Hills Road, Cambridge CB 21LA, UK). The $IC_{50}$ values measured for compounds of the formula (I) are in the range from $1 \times 10^{-5}$ to $1 \times 10^{-11}$M.

To determine the antagonistic action of the compounds of the formula (I) in vivo, their inhibiting effect on the angiotensin II-induced blood pressure increase in emedullated Sprague-Dawley rats (Möllegard, Denmark) can be measured. The blood pressure is measured in the carotid artery. I.v. administration is carried out in the penis vein. After preparation of the animal and a waiting time of 20 minutes to stabilize the hemodynamic parameters, 3 successive injections of 10, 30 and 100 ng of angiotensin II in 0.1 ml of aqueous solution are administered at 5 minute intervals. The compounds of the formula (I) are dissolved in distilled water, if necessary with addition of 10% strength ethanol and/or bases (pH<10) or acids (pH>3), and administered intravenously in doses of 1–300 μg/kg or intraduodenally in doses of 5–1000 μg/kg.

In the case of intraduodenal administration, the angiotensin II injection takes places after 20, 40 and 60 minutes, while in the case of intravenous administration the pressor response sequence takes place at 10 minute intervals.

The compounds of the formula (I) are intravenously active, in particular in the range from 1 to 300 μg/kg or intraduodenally active, in particular in the range from 5 to 300 μg/kg.

The invention also relates to pharmaceutical compositions consisting of a compound of the formula I and other active compounds, such as, for example, diuretics or non-steroidal anti-inflammatory active compounds. The compounds of the formula I can also be used as diagnostics for the renin-angiotensin system.

Pharmaceutical preparations contain an effective amount of the active compound of the formula I and possibly other active compounds together with an inorganic or organic pharmaceutically utilizable excipient. Administration can be carried out intranasally, intravenously, subcutaneously or perorally. The dosage of the active compound depends on the warm-blooded species, the body weight and age and on the manner of administration.

The pharmaceutical preparations of the present invention are prepared in a dissolving, mixing, granulating or coating process known per se.

For an oral administration form, the active compounds are mixed with the additives customary for this purpose such as excipients, stabilizers or inert diluents and brought by a customary method into suitable administration forms, such as tablets, coated tablets, hard gelatin capsules, aqueous, alcoholic or oily suspensions or aqueous, alcoholic or oily solutions. Inert carriers which can be used are, for example, gum arabic, magnesia, magnesium carbonate, potassium phosphate, lactose, glucose, magnesium stearyl fumarate or starch, in particular corn starch. In this case, the preparation can result either as dry or moist granules. Suitable oily excipients or solvents are, for example, vegetable or animal oils, such as sunflower oil and cod liver oil.

For subcutaneous or intravenous administration, the active compounds or their physiologically tolerable salts, if desired with the substances customary for this purpose such as solubilizers, emulsifiers or other auxiliaries, are made into solutions, suspensions or emulsions. Possible solvents are, for example: water, physiological saline solution or alcohols, for example ethanol, propanediol or glycerol, and in addition also sugar solutions such as glucose or mannitol solutions or alternatively a mixture of the various solvents mentioned.

According to the abovementioned process, for example, the following $IC_{50}$ values were determined for the compounds of Examples 1, 2, 3, 15, 19, 27, 31 and 51:

| Example | $IC_{50}$ [nM] |
| --- | --- |
| 1 | 78 |
| 2 | 65 |
| 3 | 149 |
| 15 | 0.8 |
| 19 | 0.74 |
| 27 | 1.1 |
| 31 | 0.48 |
| 51 | 1.8 |

List of abbreviations:

| | |
| --- | --- |
| DCI | desorption-chemical ionization |
| DMF | N,N-dimethylformamide |
| EA | ethyl acetate |
| FAB | fast atom bombardment |
| h | hour(s) |
| Hep | n-heptane |
| Min | minute(s) |
| NBS | N-bromosuccinimide |
| RT | room temperature |

EXAMPLE 1

2-n-Butyl-1-[(2-carboxy-3-chlorobenzo[b]thiophen-6-yl)-methyl]-1H-benzimidazole-7-carboxylic acid a) 2-Carboxy-6-nitrobenzamide 30 g (0.155 mol) of 3-nitrophthalic anhydride are introduced in portions into 180 ml of conc. ammonium solution and the resulting solution is heated at 100° C. with stirring for 45 min. The mixture is evaporated in a rotary evaporator and co-distilled twice with toluene, and the residue is dried in a high vacuum. It is stirred with EA, and the beige precipitate is filtered off with suction and dried in vacuo over $P_2O_5$. 31.8 g of the title compound are obtained.

Melting point: 188° C.
$R_f$ (SiO$_2$, CH$_2$Cl$_2$/MeOH 1:1)=0.3
MS (DCI): 211 (M+H)

b) 2-Amino-3-nitrobenzoic acid 31 g (0.147 mol) of the compound from Example 1a) are dissolved in 50 ml of 4N sodium hydroxide solution and 100 ml of water, 150 ml of sodium hypochlorite solution (excess on KI-starch paper) are added and the solution obtained is heated at 100° C. for 60 min. After completion of the reaction, it is cooled, treated with 250 ml of satd. Na$_2$CO$_3$ solution and 400 ml of satd. KH$_2$PO$_4$ solution, the pH of the solution is adjusted to 3 with 4N HCl/conc. HCl and the product is extracted 3 times using 500 ml of EA each time. After drying over MgSO$_4$, concentrating and stirring with diisopropyl ether, 18 g of the title compound are obtained.
Melting point: 188°–194° C.
$R_f$ (SiO$_2$, CH$_2$Cl$_2$/MeOH 1:1)=0.7
MS (DCI): 183 (M+H)

c) Methyl 2-amino-3-nitrobenzoate 18 g (99 mmol) of the compound from Example 1 b) are stirred under reflux in 200 ml of methanol with 20 ml of thionyl chloride for 48 h. The reaction solution is evaporated in a rotary evaporator, the residue is taken up in 400 ml of satd. Na$_2$CO$_3$ solution, the solution is extracted 3 times with EA, and the combined organic phases are washed with dilute Na$_2$CO$_3$ solution and satd. NaCl solution, dried over Na$_2$SO$_4$ and concentrated. Chromatography on SiO$_2$ with EA/Hep 9:1 and 7:3 yields 11.5 g of the title compound.
Melting point: 86°–88° C.
$R_f$ (SiO$_2$, EA/Hep 1:1)=0.5
MS (DCI): 197 (M+H)

d) Methyl 2-[N-(n-pentanoyl)amino]-3-nitrobenzoate 7 g (35.5 mmol) of the compound from Example 1c) are stirred at 110° C. for 1 h in 50 ml of valeryl chloride. The mixture is concentrated to dryness, the residue is treated with active carbon in ether for 30 min and filtered, the filtrate is concentrated and the residue is purified by chromatography on SiO$_2$ using EA/Hep 2:8. 5.8 g of the title compound result.
Melting point: 66°–69° C.
$R_f$ (SiO$_2$, EA/Hep 1:1)=0.4
MS (DCI): 281 (M+H)

e) 6-Bromomethyl-3-chloro-2-methoxycarbonylbenzo[b]thiophene 2.5 g (10.4 mmol) of 3-chloro-2-methoxycarbonyl-6-methylbenzo[b]thiophene (prepared according to J. Org. Chem. 41, 3399 (1976)) are boiled under reflux in 150 ml of chlorobenzene with 1.87 g of NBS and 420 mg of dibenzoyl peroxide for 5 h. After distilling off the chlorobenzene in a rotary evaporator, the residue obtained is taken up in EA, and the EA solution is washed with satd. NaHCO$_3$ solution, 10% strength Na$_2$SO$_3$ solution and satd. NaCl solution, dried over Na$_2$SO$_4$ and concentrated. Chromatography on SiO$_2$ using EA/Hep 1:20 yields 2.28 g of the title compound.
Melting point: 143°–145° C.
$R_f$ (SiO$_2$, EA/Hep 1:20)=0.3, - MS (DCI): 319, 321 (M+H)

f) Methyl 2-[N-(n-pentanoyl)-((3-chloro-2-methoxycarbonylbenzo[b]thiophen-6-yl)methyl)]amino-3-nitrobenzoate 800 mg (2.86 mmol) of the compound from Example 1d) are dissolved in 5 ml of abs. DMF, the solution is treated with 395 mg of K$_2$CO$_3$ and the mixture is stirred at room temperature for 10 min. A solution of 913 mg of the compound from Example 1e) in 20 ml of abs. DMF is added dropwise and the reaction solution is stirred overnight at room temperature. The DMF is then stripped off in vacuo, the residue is taken up in EA, and the EA phase is washed with H$_2$O, dilute, saturated NaHCO$_3$ and saturated NaCl solution, dried over Na$_2$SO$_4$ and concentrated. Chromatography on SiO$_2$ using EA/Hep 1:2 yields 860 mg of the title compound.
$R_f$ (SiO$_2$, EA/Hep 1:2)=0.3
MS(FAB): 519 (M+H)

g) Methyl 2-n-butyl-1-[(3-chloro-2-methoxycarbonylbenzo[b]thiophen-6-yl)methyl]-1H-benzimidazole-7-carboxylate 450 mg (0.85 mmol) of the compound from Example 1f) are hydrogenated in 50 ml of ethanol for 1 h in the presence of Raney nickel. The catalyst is filtered off, the filtrate is concentrated to dryness and the resulting residue is stirred at 50° C. for 30 min in 10 ml of EA/isopropanol (1:1) and 10 ml of an HCl-saturated EA solution. After concentration and crystallization from methanol, 190 mg of the title compound result.
Melting point: 167°–170° C. (dec.)
$R_f$ (SiO$_2$, CH$_2$Cl$_2$/MeOH/NH$_4$OH 49/1/0.1)=0.3
MS (DCI): 471 (M+H)

h) 2-n-Butyl-1-[(2-carboxy-3-chlorobenzo[b]-thiophen-6-yl)methyl]-1H-benzimidazole-7-carboxylic acid 185 mg (0.39 mmol) of the compound from Example 1g) are dissolved in 10 ml of ethanol, 1 ml of H$_2$O and 1 ml of conc. NaOH are added and the solution obtained is stirred at room temperature for 3 h. The EtOH is stripped off in vacuo, the aqueous solution is adjusted to a pH of 3 with glacial acetic acid and the deposited precipitate is filtered off with suction. After drying in a high vacuum, 100 mg of the title compound are obtained in the form of white crystals.
Melting point: >260° C.
$R_f$ (SiO$_2$, EA/MeOH 2/1)=0.18
MS (FAB): 443 (M+H)

EXAMPLE 2

2-n-Butyl-1-[(3-carboxy-2-phenylimidazo[1,2-a]pyridin-7-yl)methyl]-1H-benzimidazole-7-carboxylic acid a) Ethyl 2-benzoyl-2-bromoacetate 25 ml (0.144 mol) of ethyl benzoyl acetate are dissolved in 50 ml of CCl$_4$, 8.5 ml of bromine are added dropwise at 5° C. and the brown solution is stirred at 5° C. for 1 h, at room temperature for 3 h and at 60° C. for 2 h. It is concentrated to dryness, the residue is taken up in EA, the EA solution is washed with 10% strength Na$_2$SO$_3$ solution and satd. NaCl solution, dried over MgSO$_4$ and concentrated, and the residue is dried in a high vacuum. 38 g of the title compound result as a red oil.
$R_f$ (SiO$_2$, EA/Hep 1/6)=0.28
MS (DCI): 271, 273 (M+H)

b) Ethyl 7-methyl-2-phenylimidazo[1,2-a]pyridine-3-carboxylate 38 g (0.14 mol) of the compound from Example 2a) and 15.2 g of 2-amino-4-methylpyridine are stirred in ethanol for 8 h under reflux. The mixture is concentrated to dryness, the residue is treated with satd. $Na_2CO_3$ solution and extracted several times with EA, and the combined organic phases are washed with satd. NaCl, dried over $Na_2SO_4$ and concentrated. Chromatography on $SiO_2$ using EA/Hep 2:1 yields 12.2 g of the title compound.

$R_f$ ($SiO_2$, EA/Hep 2:1)=0.3
MS (DCI): 281 (M+H)

c) Ethyl 7-bromomethyl-2-phenylimidazo[1,2-a]-pyridine-3-carboxylate 3 g (10.7 mmol) of the compound from Example 2b) are brominated with 1.27 g of NBS and 150 mg of benzoyl peroxide by the process given in Example 1e). 1.2 g of the title compound result.

$R_f$ ($SiO_2$, EA/Hep 1/2)=0.2
MS (DCI): 259, 361 (M+H)

d) Methyl 2-[N-(n-pentanoyl)-(3-ethoxycarbonyl-2-phenylimidazo[1,2-a]pyridin-7-yl )methyl]amino-3-nitrobenzoate 800 mg (2.85 mmol) of the compound from Example 1d), 1.03 g of the compound from Example 2c) and 400 mg of $K_2CO_3$ are reacted by the process mentioned in Example 1f). 520 mg of the title compound result.

$R_f$ ($SiO_2$, EA/Hep 1:1)=0.2
MS (FAB): 559 (M+H)

e) Methyl 2-n-butyl-1-[(3-ethoxycarbonyl-2-phenylimidazo[1,2-a]pyridin-7-yl)methyl]-1H-benzimidazole-7-carboxylate 400 mg (0.71 mmol) of the compound from Example 2d) are reacted by the process mentioned in Example 1g). After precipitation from methanol using diethyl ether, 250 mg of the title compound result.

Melting point: 217°–220° C. (dec.)
$R_f$ ($SiO_2$, EA/Hep 9/1)=0.5
MS (DCI): 511 (M+H)

f) 2-n-Butyl-1-[(3-carboxy-2-phenylimidazo[1,2-a]-pyridin-7-yl)methyl]-1H-benzimidazole-7-carboxylic acid 230 mg (0.45 mmol) of the compound from Example 1e) are hydrolyzed by the process given in Example 1h). 117 mg of the title compound in the form of white crystals result.

Melting point: 202°–204° C.
$R_f$ ($SiO_2$, EA/MeOH 2/1)=0.1
MS (FAB): 469 (M+H)

EXAMPLE 3

2-n-Butyl-1-[(3-carboxy-2-phenylimidazo[1,2-a]pyrimidin-7-yl)methyl]-1H-benzimidazole-7-carboxylic acid a) Ethyl 7-methyl-2-phenylimidazo[1,2-a]pyrimidine-3-carboxylate

The title compound is prepared by the process described in Example 2b) from the compound of Example 2a) and 2-amino-4-methylpyrimidine.

$R_f$ ($SiO_2$, EA/Hep 2:1)=0.2
MS (DCI): 282 (M+H)

b) Ethyl 7-bromomethyl-2-phenylimidazo[1,2-a]-pyrimidine-3-carboxylate

This compound is prepared by the process mentioned in Example 2c); from 2 g (7.11 mmol) of the compound of Example 3a), 510 mg of the title compound result.

$R_f$ ($SiO_2$, EA/Hep 1:2)=0.2
MS (FAB): 360, 362 (M+H)

c) Methyl 2-[N-(n-pentanoyl)-(3-ethoxycarbonyl-2-phenylimidazo[1,2-a]pyrimidin-7-yl)methyl]-amino-3-nitrobenzoate This compound is prepared by the process of Example 1f). From 435 mg (1.55 mmol) of the compound from Example 1d) and 558 mg of the compound from Example 3b), 550 mg of the title compound are obtained.

$R_f$ ($SiO_2$, EA/Hep 2:1)=0.2
MS (DCI): 560 (M+H)

d) Methyl 2-n-butyl-1-[(3-ethoxycarbonyl-2-phenylimidazo[1,2-a]pyrimidin-7-yl)methyl]-1H-benzimidazole-7-carboxylate This compound is prepared by the process mentioned in Example 1g); from 380 mg (0.68 mmol) of the compound of Example 3c), 102 mg of the title compound result as a slightly beige, crystalline residue.

Melting point=185°–187° C.
$R_f$ ($SiO_2$, EA/Hep 1:1)=0.2
MS (FAB): 512 (M+H)

e) 2-n-Butyl-1-[(3-carboxy-2-phenylimidazo[1,2-a]-pyrimidin-7-yl)methyl]-1H-benzimidazole-7-carboxylic acid This compound is prepared by the process mentioned in Example 1h). From 45 mg (0.09 mmol) of the compound of Example 3d), 31 mg of the title compound are obtained.

Melting point: >260° C.
$R_f$ ($SiO_2$, EA/MeOH)=0.1
MS (FAB): 470 (M+H)

EXAMPLE 4

2-n-Butyl-3-[(2-carboxy-3-chlorobenzo[b]thiophen-6-yl)-methyl]-3H-imidazo[4,5-b]pyridine a) 2-n-Butyl-3H-imidazo[4,5-b]pyridine 10 g (91.6 mmol) of 2,3-diaminopyridine and 27.4 g of valeric acid are stirred at 170° C. for 18 h. After completion of the reaction, the mixture is diluted with 100 ml of $CH_2Cl_2$, washed with saturated $NaHCO_3$ solution, water and saturated NaCl solution, dried over $Na_2SO_4$ and concentrated. Chromatography on $SiO_2$ using EA/Hep 20:1 yields 9.7 g of the title compound.

Melting point: 103° C.
$R_f$ ($SiO_2$, EA/MeOH 20:1)=0.3
MS (DCI): 176 (M+H)

b) 2-n-Butyl-3-[(3-chloro-2-methoxycarbonylbenzo[b]thiophen-6-yl)methyl]-3H-imidazo[4,5-b]-pyridine 300 mg (0.94 mmol) of the compound from Example 1e) and 175 mg of the compound from Example 4a) are stirred at room temperature for 8 h with 552 mg of $K_2CO_3$ in 10 ml of DMF. The mixture is concentrated to dryness, the residue is taken up in EA, and the EA solution is washed with $H_2O$, dilute $KHSO_4$ solution, saturated $NaHCO_3$ solution and saturated NaCl solution, dried over $Na_2SO_4$, and concentrated. Chromatography on $SiO_2$ using EA/Hep 1:1 yields 130 mg of the title compound as a slightly yellow powder.

Melting point: 127°–129° C.
$R_f$ ($SiO_2$, EA/Hep 1:1)=0.2
MS (DCI): 414 (M+H)

c) 2-n-Butyl-3-[(2-carboxy-3-chlorobenzo[b]-thiophen-6-yl)methyl]-3H-imidazo[4,5-b]pyridine 117 mg (0.28 mmol) of the compound from Example 4b) are reacted by the process mentioned in Example 1h). 107 mg of the title compound result as a white powder.

Melting point: >260° C.
$R_f$ ($SiO_2$, EA/MeOH 2:1)=0.3
MS (FAB): 400 (M+H)

EXAMPLE 5

2-n-Butyl-3-[(3-carboxy-2-phenylimidazo[1,2-a] pyridin-7-yl)methyl]-3H-imidazo[4,5-b]pyridine a) 2-n-Butyl-3-[(3-ethoxycarbonyl-2-phenylimidazo-[1,2-a]pyridin-7-yl)methyl]-3H-imidazo[4,5-b]-pyridine The title compound is prepared by the process mentioned in Example 4b) from the compounds of Examples 2c) and 4a).

MS (DCI): 454 (M+H)

b) 2-n-Butyl-3-[(3-carboxy-2-phenylimidazo[1,2-a]-pyridin-7-yl)methyl]-3H-imidazo[4,5-b]pyridine The title compound is prepared by the process given in Example 1h) from the compound of Example 5a).

MS(FAB): 426 (M+H)

EXAMPLE 6

2-n-Butyl-3-[(3-carboxy-2-phenylimidazo[1,2-a] pyrimidin-7-yl)methyl]-3H-imidazo[4,5-b]pyridine a) 2-n-Butyl-3-[(3-ethoxycarbonyl-2-phenylimidazo-[1,2-a]pyrimidin-7-yl)methyl]-3H-imidazo[4,5-b)-pyridine This compound is prepared from the compounds of Examples 3b) and 4a) by the process of Example 4b).

MS (DCI): 455 (M+H)

b) 2-n-Butyl-3-[(3-carboxy-2-phenylimidazo[1,2-a]-pyrimidin-7-yl)methyl]-3H-imidazo[4,5-b]-pyridine The title compound results from the compound of Example 6a) by the reaction described in Example 1h).

MS(FAB): 427 (M+H)

EXAMPLE 7

2-n-Butyl-3-[2-(4-methylphenyl)-3-(1H-tetrazol-5-yl)imidazo[4,5-b]pyridinyl]-3H-imidazo[4,5-b] pyridine a) 2-(4-Methylphenyl)imidazo[4,5-a]pyridine 8.6 g (91.4 mmol) of 2-aminopyridine and 7.7 g (45.7 mmol) of chloromethyl p-tolyl ketone (prepared according to Chem. Lett., 1990, 1125–1128) are stirred at 130° C. for 45 min. The reaction solution is then diluted with $CH_2Cl_2$, washed with water and saturated NaCl solution, dried over $MgSO_4$ and concentrated. Chromatography on $SiO_2$ using EA/Hep 4:1→1:1 yields 6.8 g of the title compound.

Melting point: 142°–144° C.
$R_f$ ($SiO_2$, EA/Hep 1:1)=0.2
MS (DCI): 209 (M+H)

b) 3-Formyl-2-(4-methylphenyl)imidazo[4,5-a]-pyridine 21 ml (0.27 mol) of DMF are treated with 3.6 ml of $POCl_3$ in 60 ml of $CH_2Cl_2$ at 0° C., the reaction solution is stirred at room temperature for 30 min and a solution of 6.8 g (32.7 mmol) of the compound from Example 7a) is added dropwise at 0° C. After stirring for 2 h at 60° C., the mixture is concentrated, the residue is treated with a solution of 20 g of NaOH in 200 ml of $H_2O$ and stirred under reflux for 1 h, and the precipitate which deposits after cooling in an ice bath is filtered off with suction. Recrystallization from ethanol yields 5.5 g of the title compound.

Melting point: 168°–171° C.
$R_f$ ($SiO_2$, EA/Hep 8:2)=0.4
MS (DCI): 237 (M+H)

c) 3-Hydroximino-2-(4-methylphenyl)imidazo[4,5-a]-pyridine 2 g (8.47 mmol) of the compound of Example 7b) are treated in 130 ml of methanol with a solution of 883 mg of hydroxylamine hydrochloride and 1.04 g of sodium acetate in 65 ml of water. The reaction solution is stirred at room temperature for 5 h and under reflux for 1 h. The methanol is stripped off in the rotary evaporator, then the residue is diluted with water and the precipitate which deposits after cooling is filtered off with suction. After drying over $P_2O_5$ in a high vacuum, 2.04 g of the title compound result.

Melting point: 202°–206° C.
$R_f$ ($SiO_2$, EA/Hep 1:1)=0.3
MS (DCI): 252 (M+H)

d) 3-Cyano-2-(4-methylphenyl)imidazo[4,5-a] pyridine 2.1 g (9.0 mmol) of the compound from Example 7c) are introduced in portions, with ice-cooling and stirring, into 45 ml of thionyl chloride and the reaction solution is stirred at room temperature for 45 min. The thionyl chloride is distilled off twice from toluene, the residue is taken up in EA, and the EA solution is washed with satd. $Na_2CO_3$ and satd. NaCl solution, dried over $MgSO_4$ and concentrated. Recrystallization from diisopropyl ether/EA yields 1.9 g of the title compound.

Melting point: 138°–144° C.
$R_f$ ($SiO_2$, EA/Hep 1:1)=0.2
MS (DCI): 234 (M+H)

e) 2-(3-Bromomethylphenyl)-3-cyanoimidazo[4,5-a] pyridine

This compound is prepared by the process mentioned in Example 1e). From 1.7 g of the compound of Example 7d), 1.73 g of the title compound result.

Melting point: 182°–186° C.
$R_f$ ($SiO_2$, EA/Hep 1:1)=0.2
MS (DCI): 312/314 (M+H)

f) 2-n-Butyl-3-[3-cyano-2-(4-methylphenyl)imidazo-[4,5-a]pyridinyl]-3H-imidazo[4,5-b]pyridine The title compound is prepared from the compounds of Examples 4a) and 7e) by the process mentioned in Example 4b).

MS (DCI): 407 (M+H)

g) 2-n-Butyl-3-[2-(4-methylphenyl)-3-(1H-tetrazol-5-yl)imidazo[4,5-b]pyridinyl]-3H-imidazo[4,5-b]-pyridine 210 mg (0.51 mmol) of the compound from Example 7f) are stirred under reflux in 5 ml of toluene with 308 mg of trimethyltin azide for 3 days. The reaction solution is diluted with 4 ml of ether and, after addition of 7 ml of saturated KF solution and 0.2 ml of HBF$_4$ solution (50% strength), stirred at room temperature for 2 days. The mixture is diluted with EA and filtered, and the organic phase of the filtrate is separated off, washed with H$_2$O and saturated NaCl solution, dried over Na$_2$SO$_4$ and concentrated. Chromatography on SiO$_2$ using EA/MeOH 3:1 yields 110 mg of the title compound.

MS (FAB): 450 (M+H)

EXAMPLE 8

2-n-Butyl-1-[2-(4-methylphenyl)-3-(1H-tetrazol-5-yl)imidazo[4,5-a]pyridinyl]-1H-benzimidazole-7-carboxylic acid a) Methyl 2-[N-(n-pentanoyl)-(3-cyano-2-(4-methylphenyl)imidazo[4,5-a]pyridinyl]amino-3-nitrobenzoate This compound is prepared from the compounds of Examples 1d) and 7e) by the process given in Example 1f). In this process, from 730 mg (2.34 mmol) of the compound from Example 7e) and 655 mg (2.34 mmol) of the compound from Example 1d), 988 mg of the title compound result.

Melting point: 128°–131° C.
R$_f$ (SiO$_2$, EA/Hep 8:2)=0.3
MS (DCI): 512 (M+H)

b) Methyl 2-n-Butyl-1-[3-cyano-2-(4-methylphenyl)imidazo[4,5-a]pyridinyl]-1H-benzimidazole-7-carboxylate The title compound is prepared from the compound of Example 8a) by the process of Example 1g).

R$_2$ (SiO$_2$, CH$_2$Cl$_2$/MeOH 95:5)=0.2
MS (DCI): 464 (M+H)

c) Methyl 2-n-butyl-1-[2-(4-methylphenyl)-3-(1H-tetrazol-5-yl)imidazo[4,5-a]pyridinyl]-1H-benzimidazole-7-carboxylate 157 mg (0.34 mmol) of the compound from Example 8b) are reacted by the process mentioned in Example 7g); 88 mg of the title compound result.

Melting point: 120°–155° C.
R$_f$ (SiO$_2$, CH$_2$Cl$_2$/MeOH 8:2)=0.3
MS (FAB): 507 (M+H)

d) 2-n-Butyl-1-[2-(4-methylphenyl)-3-(1H-tetrazol-5-yl)imidazo[4,5-a]pyridinyl]-1H-benzimidazole 7-carboxylic acid The title compound is prepared from the compound of Example 8b) by the process mentioned in Example 1h).

R$_f$ (SiO$_2$, CH$_2$Cl$_2$/MeOH(AcOH/H$_2$O 20:15:2:4)=0.8
MS (FAB): 493 (M+H)

EXAMPLE 9

5,7-Dimethyl-2-ethyl-3-(2-carboxy-3-chlorobenzo[b]-thiophen-6-yl)-methyl]-3H-imidazo[4,5-b]pyridine a) 5,7-Dimethyl-2-ethyl-3-[(3-chloro-2-methoxycarbonylbenzo[b]thiophen-6-yl)methyl]-3H-imidazo[4,5-b]pyridine 500 mg (2.8 mmol) of 5,7-dimethyl-2-ethyl-3H-imidazo [4,5-b]pyridine (disclosed in MP-A 400,974) are treated under argon in 10 ml of abs. DMF with 165 mg of NaH (50% strength), 900 mg (2.8 mmol) of the compound from Example 4b) are added to the reaction solution, after 30 min and the mixture is stirred at room temperature for 2 h. The reaction solution is treated with water and extracted with EA, and the combined EA extracts are washed with water and satd. NaC solution, dried over MgSO$_4$ and concentrated. Chromatography on SiO$_2$ using EA/MeOH 15:1 yields 700 mg of the title compound.

R$_f$ (SiO$_2$, EA/MeOH 15:1)=0.3
MS (DCI): 414 (M+H)

b) 5,7-Dimethyl-2-ethyl-3-[(2-carboxy-3-chlorobenzo[b]thiophen-6-yl)methyl]-3H-imidazo[4,5-b]pyridine 680 mg (1.64 mmol) of the compound from Example 9a) are reacted by the process mentioned in Example 1h). 570 mg of the title compound result.

MS (DCI): 400 (M+H)

EXAMPLE 10

5,7-Dimethyl-2-ethyl-3-[(3-carboxy-2-phenylimidazo[1,2-a]pyridin-7-yl)methyl]-3H-imidazo[4,5-b]pyridine a) 5,7-Dimethyl-2-ethyl-3-[(3-ethoxycarbonyl-2-phenylimidazo[1,2-a]pyridin-7-yl)methyl]-3H-imidazo[4,5-b]pyridine This compound is prepared from 5,7-dimethyl-2-ethyl-3H-imidazo[4,5-b]pyridine analogously to the process given in Example 9a) (prepared according to EP-A 400,974) and the compound from Example 2c). From 280 mg (0.78 mmol) of the compound from Example 2c), 160 mg of the title compound result.

R$_f$ (SiO$_2$, EA)=0.2
MS (FAB): 454 (M+H)

b) 5,7-Dimethyl-2-ethyl-3-[(3-carboxy-2-phenylimidazo[1,2-a]pyridin-7-yl)methyl]-3H-imidazo[4,5-b]pyridine The title compound is prepared from the compound of Example 10b) by the process mentioned in Example 1h).
MS (FAB): 426 (M+H)

EXAMPLE 11

5,7-Dimethyl-2-ethyl-3-[(2-(4-methylphenyl)-3-(1H-tetrazol-5-yl)imidazo[4,5-a]pyridinyl)-3H-imidazo[4,5]pyridine a) 5,7-Dimethyl-2-ethyl-3-[3-cyano-2-(4-methylphenyl)imidazo[4,5-a]pyridinyl)-3H-imidazo[4,5]pyridine The title compound is prepared from 5,7-dimethyl-2-ethyl-3H-imidazo[4,5-b]pyridine (prepared according to EP-A 400,974) and the compound from Example 7e).

MS (DCI), 407 (M+H)

b) 5,7-Dimethyl-2-ethyl-3-[(2-(4-methylphenyl)-3-(1H-tetrazol-5-yl)imidazo[4,5-a]pyridinyl)-3H-imidazo[4,5-b]pyridine The title compound is prepared from the compound of Example 11a) by the process mentioned in Example 7g).
MS(FAB), 450 (M+H)

EXAMPLE 12

3-[(2'-Aminoethylphenyl)carbonylaminosulfonylbiphenyl-4-yl)methyl]-5,7-dimethyl-2-ethyl-3H-imidazo[4,5-b]pyridine a) Sulfonamidobromobenzene 51.6 g (0.3 mol) of o-bromoaniline are added under an argon atmosphere to a solution of 100 ml of conc. HCl and 30 ml of glacial acetic acid, a solution of 22.4 g of sodium nitrite in 30 ml of water is added dropwise at −10° C. and the reaction solution is stirred at −5° C. for 60 min. The solution obtained is added dropwise to an $SO_2$-saturated solution of 7 g of $CuCl_2.2H_2O$ and 0.5 g of CuCl in 300 ml of glacial acetic acid. After stirring at room temperature for 60 min, the mixture is poured into an ice/water mixture and extracted with ether, and the ether extracts are washed with satd. $NaHCO_3$ solution and water, dried over $MgSO_4$ and concentrated. The 67.8 g of sulfonyl chloride compound obtained are treated with 300 ml of conc. ammonia with cooling in 500 ml of acetone. After stripping off the acetone, the resulting suspension is diluted with water, and the white crystals which deposit are filtered off with suction, washed with $H_2O$ and dried in a high vacuum. The title compound is employed without further purification in the following reaction.

b) 2,N,N-Dimethylaminoformylsulfonamidobromobenzene 0.236 mol of the compound from Example 12a) is stirred at room temperature for 2 h with 40 ml of N,N-dimethylformamide dimethyl acetal in 150 ml of abs. DMF. The reaction solution is poured into 200 ml of 5% strength $NaHSO_4$ solution/ice (1:1), and the precipitate which deposits is filtered off with suction, washed with $H_2O$ and dried in vacuo. 67 g of the title compound are obtained.
$R_f$ ($SiO_2$, EA/Hep 1:1)=0.1
MS (DCI), 291/293 (M+H)

c) 4'-Methylbiphenyl-N,N-dimethylaminoformylsulfonamide

To 11 g (37.9 mmol) of the compound from Example 12b), 1 g of triphenylphosphine, and 8 g of $Na_2CO_3$ in 150 ml of toluene and 40 ml of $H_2O$, first 420 mg of $Pd(OAc)_2$ and then 5.66 g (41.9 mmol) of tolylboronic acid in 100 ml of ethanol are added under argon. The mixture is now heated to boiling for 4 h, then concentrated and taken up in 500 ml of EA and 500 ml of $H_2O$. The resulting precipitate is filtered off and characterized as the title compound. The EA phase is separated off, dried over $Na_2SO_4$ and concentrated. Chromatography on $SiO_2$ using EA yields a further amount of the title compound; total yields 7.6 g.
$R_f$ ($SiO_2$, EA/Hep 1:1)=0.2
MS (DCI): 303 (M+H)

d) 4'-Bromomethylbiphenyl-2-N,N-dimethylaminoformylsulfonamide

The title compound is prepared from the compound 12c) by the process of Example 1e). In this process, 1.2 g of the title compound result from 3.8 g (13.5 mmol) of the compound 12c).

$R_f$ ($SiO_2$, EA/Hep 2:1)=0.2
MS (DCI): 381/383 (M+H)

e) 5,7-Dimethyl-3-[(2'-N,N-dimethylaminoformylsulfonamidobiphenyl-4-yl)methyl]-2-ethyl-3H-imidazo[4,5-b]pyridine The title compound is prepared from the compound of Example 12d) and 5,7-dimethyl-2-ethyl-3H-imidazo[4,5-b]pyridine by the process of Example 9a). 1.1 g of the title compound is obtained from 3.2 g of the compound 12d).
$R_f$ ($SiO_2$, EA/MeOH 10.1)=0.2
MS (FAB): 476 (M+H)

f) 5,7-Dimethyl-2-ethyl-3-[(2'-sulfonamidobiphenyl-4-yl)methyl]-3H-imidazo[4,5-b]pyridine 0.6 g (1.26 mmol) of the compound from Example 12e) is boiled under reflux in 20 ml of ethanol with 10 ml of conc. HCl solution for 45 min. The ethanol is removed in vacuo, and the residue is neutralized with saturated $NaHCO_3$ solution, adjusted to pH~5–6 with $NaHSO_4$ solution and extracted with EA. The EA phase is dried ($Na_2SO_4$) and concentrated, 380 mg of the title compound being obtained.
$R_f$ ($SiO_2$, EA/Hep 5:1)=0.5
MS (FAB): 421 (M+H)

g) 5,7-Dimethyl-2-ethyl-3-[(2'-ethoxycarbonylaminosulfonylbiphenyl-4-yl)methyl]-3H-imidazo[4,5-b]pyridine 0.52 g (1.2 mmol) of the compound from Example 12f) and 340 mg of $K_2CO_3$ are heated under reflux under argon for 3 h with 266 mg (2.4 mmol) of ethyl chloroformate in 10 ml of dry DMF. After cooling to room temperature, the mixture is treated with 10% $NaHSO_4$ and extracted with EA, and the organic phase is dried over $MgSO_4$. Concentration and chromatography on $SiO_2$ using EA as the eluent yield 250 mg of the title compound.
$R_f$ ($SiO_2$, EA)=0.2
MS (FAB): 493 (M+H)

h) 3-[(2'-(Aminoethylphenyl)carbonylaminosulfonylbiphenyl-4-yl)methyl]-5,7-dimethyl-2-ethyl-3-imidazo[4,5-b]pyridine 80 mg (0.16 mmol) of the compound from Example 12g) and 50 µl of phenylethylamine are boiled under reflux in 5 ml of abs. toluene under argon for 1.5 h. After concentration and chromatography on $SiO_2$ using EA/MeOH 10:1, 70 mg of the title compound result after freeze-drying as an amorphous powder.
$R_f$ ($SiO_2$, EA/MeOH 10:1)=0.4
MS (FAB): 568 (M+H)

EXAMPLE 13

3-[(2'-Aminomethylcyclohexyl)carbonylaminosulfonylbiphenyl-4-yl)methyl]-5,7-dimethyl-2-ethyl-3H-[4,5-b]pyridine The title compound is prepared by the process of Example 12h) from the compound of Example 12g) and cyclohexylmethylamine; from 80 mg (0.16 mmol) of Example 12g), 90 mg of the title compound results after freeze-drying as an amorphous solid.
$R_f$ ($SiO_2$, EA)=0.3
MS (FAB): 560 (M+H)

EXAMPLE 14

3-[(2'-Diallylamino)carbonylaminosulfonylbiphenyl-4-yl)methyl]-5,7-dimethyl-2-ethyl-3H-imidazo[4,5-b]pyridine The title compound is prepared by the process of Example 12h) from the compound of Example 12g) and diallylamine. 60 mg of the title compound result from 80 mg (0.16 mmol) of Example 12g) as an amorphous solid.

$R_f$ (SiO$_2$, EA/MeOH 10:1)=0.2
MS (FAB): 544 (M+H)

EXAMPLE 15

3-[(2'-N,N-Diallyloxycarbonyl) aminosulfonylbiphenyl-4-yl)methYl]-5,7-dimethyl-2-ethyl-3H-imidazo[4,5-b]pyridine 100 mg (0.23 mmol) of the compound from Example 12f) are heated to boiling for 45 min in 10 ml of abs. DMF under argon with 66 mg (0.46 mmol) of K$_3$CO$_3$ and 57 mg (0.46 mmol) of allyl chloroformate. After concentrating, taking up in EA, washing the EA phase with 10% strength Na$_2$HSO$_4$ solution, drying (MgSO$_4$) and chromatography on SiO$_2$ using EA, 70 mg of the title compound result after freeze-drying.

$R_f$ (SiO$_2$, EA)=0.6
MS (FAB): 589 (M+H)

EXAMPLE 16

3-[(2'-(N,N-Dibenzyloxycarbonyl) aminosulfonylbiphenyl-4-yl)methyl]-5,7-dimethyl-2-ethyl-3H-imidazo[4,5-b]pyridine This compound is prepared by the process of Example 15 from the compound of Example 12f) and benzyl chloroformate. From 100 mg (0.23 mmol) of the compound 12f), 70 mg of the title compound result.

$R_f$ (SiO$_2$, EA)=0.2
MS (FAB): 689 (M+H)

EXAMPLE 17

3-[(2'-(Cyclohexylmethoxycarbonyl) aminosulfonylbiphenyl-4-yl)methyl]-5,7-dimethyl-2-ethylimidazo[4,5-b]pyridine The title compound is prepared from the compound of Example 12f) and cyclohexylmethyl chloroformate by the process of Example 15, amide and ester being employed, however, in an equimolar ratio.

$R_f$ (SiO$_2$, methyl tert-butyl ether)=0.2
MS (FAB): 561 (M+H)

EXAMPLE 18

5,7-Dimethyl-2-ethyl-3-(2'-(ethyloxycarbonyl) aminosulfonylbiphenyl-4-yl)methyl]-3H-imidazo[4,5-b]pyridine The title compound results from the compound of Example 12f) and ethyl chloroformate by the process of Example 17.

$R_f$ (SiO$_2$, EA)=0.2
MS (FAB): 493 (M+H)

EXAMPLE 19

2-n-Butyl-1-[(2'-ethoxycarbonylaminosulfonylbiphenyl-4-yl)methyl]-1H-benzimidazole-7-carboxylic acid a) Methyl 2-[N-(n-pentanoyl)-((2'-N,N-dimethylaminoformylsulfonamidobiphenyl-4-yl) methyl)]amino-3nitrobenzoate 7.9 g (28.2 mmol) of the compound from Example 1d) are stirred at room temperature for 24 h with 10.7 g (28.2 mmol) of the compound from Example 12d) and 11.7 g (84.6 mmol) of K$_2$CO$_3$ in 200 ml of abs. DMF. The mixture is then concentrated to dryness, the residue is taken up in EA, and the EA solution is washed 3× with H$_2$O, 1× with KHSO$_4$ solution (25% strength), 1× with saturated NaHCO$_3$ solution and 1× with saturated NaCl solution, dried over MgSO$_4$ and concentrated. The oily residue yields 7.9 g of the title compound after crystallization from EA/diisopropyl ether. Chromatography of the concentrated mother liquor on SiO$_2$ using n-heptane/EA (2:3) yielded a further 2.54 g of the title compound.

Melting point: 148°–152° C.
$R_f$ (SiO$_2$, n-heptane/EA 2:8)=0.33
MS (FAB): 581 (M+H)

b) Methyl 2-[N-(n-pentanoyl)-((2'-N,N-dimethylaminoformylsulfonamidobiphenyl-4-yl) methyl]amino-3-aminobenzoate 10.4 g (17.9 mmol) of the compound from, Example 19a) are hydrogenated in 800 ml of methanol for 3h in the presence of Raney nickel. The catalyst is filtered off, the filtrate is concentrated to dryness and the residue is dried in a high vacuum. 9.9 g of the title compound result as an amorphous foam.

$R_f$ (SiO$_2$, CH$_2$Cl$_2$/MeOH 95:5)=0.3
MS(FAB): 551 (M+H)

c) Methyl 2-n-butyl-1-[(2'-sulfonamidobiphenyl-4-yl)methyl]-1H-benzimidazole-7-carboxylate 9.8 g (17.8 mmol) of the compound from Example 19h) are stirred under reflux for 3h with 90 ml of concentrated hydrochloric acid in 180 ml of methanol. The solvent is evaporated, the remaining solution is adjusted to pH ~5–6 with 6N NaOH solution, the aqueous solution is extracted 3× with CH$_2$Cl$_2$, and the combined organic phases are washed with saturated NaCl solution and dried over MgSO$_4$. Recrystallization from EA yielded 8.16 g of the title compound in the form of white crystals.

Melting point: 192°–195° C.
$R_f$ (SiO$_2$, EA/n-heptane 8:2)=0.38
MS (FAB)=478 (M+H)

Alternatively, the title compound also results by this process from the compound from Example 19a). In this case, 60 mg of the desired compound are obtained from 100 mg (0.19 mmol) of the compound from 19a).

d) Methyl 2-n-butyl-1-[(2'-dimethylaminoformylsulfonamidobiphenyl-4-yl) methyl]-1H-benzimidazole-7-carboxylate 150 mg (0.18 mmol) of the compound from Example 19b) are allowed to stand at room temperature over night with 10 ml of an HCl-saturated EA solution in 10 ml of isopropanol/EA (1:1) under argon. The mixture is concentrated, the residue is taken up in CH$_2$Cl$_2$, and the CH$_2$Cl$_2$ phase is washed with saturated Na$_2$-CO$_3$ solution, water and saturated NaCl solution and dried over MgSO$_4$. Concentration and drying in a high vacuum yield 138 mg of the title compound as an amorphous foam.

$R_f$ (SiO$_2$, CH$_2$Cl/MeOH 95:5)=0.5
MS (FAB): 533 (M+H)

e) Methyl 2-n-butyl-1-[(2'-ethoxycarbonylaminosulfonylbiphenyl-4-yl)-methyl] -1H-benzimidazole-7-carboxylate 3.25 g (6.81 mmol) of the compound from Example 19c) and 170 mg (1.36 mmol) of DMAP are treated in 12 ml of absolute pyridine under argon at 0° C. with 1.53 g (13.6 mmol) of K-tert-butylate and, after stirring for 10 minutes at the same temperature, with 0.65 ml (6.81 mmol) of ethyl chloroformate. The mixture is stirred over night at room temperature. The solution is then adjusted with a 25% strength $KHSO_4$ solution with ice-cooling until it gives an acidic reaction and extracted several times with EA. The combined organic phases are washed with saturated NaCl solution, dried over $MgSO_4$ and concentrated. Chromatography on $SiO_2$ using $CH_2Cl_2/MeOH/NH_3$ (9:1:0.1) yielded 1.8 g of the title compound as an amorphous foam.

$R_f$ ($SiO_2$, $CH_2Cl_2$/MeOH/HOAC 9:1:0.2)=0.71
MS (FAB): 550 (M+H)

f) Methyl 2-n-butyl-1-[(2'-ethoxycarbonylaminosulfonylbiphenyl-4-yl)methyl]-1H-benzimidazole-7-carboxylic acid The preparation of the title compound from the compound from Example 19e) is carried out by the process given in Example 1h).

$R_f$ ($SiO_2$, $CH_2Cl_2$/MeOH/HOAC 9:1:0.2)=0.64
MS (FAB): 536 (M+H)

EXAMPLE 20

2-n-Butyl-1-[(2'-n-proylaminocarbonylaminosulfonylbiphenyl-4-yl)methyl]-1H-benzimidazole-7-carboxylic acid a) Methyl 2-n-butyl-1-[(2'-n-propylaminocarbonylaminosulfonylbiphenyl-4-yl)methyl]-1H-benzimidazole-7-carboxylate 100 mg (0.21 mmol) of the compound from Example 19c) are boiled under reflux in 8 ml of absolute acetone with 90 mg (0.6 mmol) of $K_2CO_3$ in 24 µl (0.25 mmol) of n-propyl isocyanate for 2 h. After cooling, the solution is adjusted to pH~1 by addition of 2N HCl and extracted several times with $CH_2Cl_2$. The combined organic phases are washed 1× with $H_2O$ and 1× with saturated NaCl solution, dried over $MgSO_4$ and concentrated. Recrystallization from EA yields 107 mg of the title compound.

Melting point: 150°–152° C.
$R_f$ ($SiO_2$, $CH_2Cl_2$/MeOH/$NH_3$ 9:10.2)=0.24
MS (FAB): 563 (M+H)

b) Methyl 2-n-butyl-1-[(2'-n-propylaminocarbonylaminosulfonylbiphenyl-4-yl)-methyl]-1H-benzimidazole-7-carboxylic acid The title compound is prepared from the compound from Example 20a) by the process mentioned in Example 1b). 30 mg of the desired compound are obtained from 38 mg (0.07 mmol) of 20a) as an amorphous foam.

$R_f$ ($SiO_2$, $CH_2Cl_2$/MeOH/ACOH 9:1:0.2)=0.2
MS (FAB): 549 (M+H)

EXAMPLE 21

2-n-Butyl-1-[(2'-ispropylaminocarbonylaminosulfonylbiphenyl-4-yl)-methyl]-1H-benzimidazole-7-carboxylic acid 206 mg (0.38 mmol) of the compound from Example 19e) are reacted at 80° C. in an autoclave for 8 h with 5 ml of isopropylamine in 50 ml of toluene. The reaction solution is concentrated and the residue is chromatographed on $SiO_2$ using $CH_2Cl_2$/MeOH (95:5). 38 mg of the title compound result as an amorphous foam.

$R_f$ ($SiO_2$, $CH_2Cl_2$/MeOH/ACOH 9:1:0.2)=0.35
MS (FAB): 549 (M+H)

EXAMPLE 22

2-n-Butyl-1-[(2'-allylaminocarbonylaminosulfonylbiphenyl-4-yl)-methyl]-1M-benzimidazole-7-carboxylic acid a) Methyl 2-n-butyl-1-[(2'-allylaminocarbonylaminosulfonylbiphenyl-4-yl)-methyl]-1H-benzimidazole-7-carboxylate The title compound is prepared from the compound from Example 19c) by the process of Example 20a) using allyl isocyanate instead of n-propyl isocyanate. 136 mg of the title compound result from 150 mg (0.31 mmol) of 19c).

Melting point: 142°–145° C.
$R_f$ ($SiO_2$, $CH_2Cl_2$/MeOH/$NH_3$ 9:1:0.2)=0.19
MS (FAB): 561 (M+H)

b) 2-n-Butyl-1-[(2'-allylaminocarbonylaminosulfonylbiphenyl-4-yl)-methyl]-1H-benzimidazole-7-carboxylic acid The preparation of this compound was carried out by the process of Example 1h) and yielded 73 mg of the title compound from 123 mg (0.22 mmol) of the compound from 22a).

Melting point: 220° C.
$R_f$ ($SiO_2$, $CH_2Cl_2$/MeOH/ACOH 9:1:0.2)=0.35
MS (FAB): 547 (M+H)

EXAMPLE 23

2-n-Butyl-1-[(2'-ethylaminocarbonylaminosulfonylbiphenyl-4-yl)-methyl]-1H-benzimidazole-7-carboxylic acid a) Methyl-2-n-butyl-1-[(2'-ethylaminocarbonylaminosulfonylbiphenyl-4-yl)-methyl]-1H-benzimidazole-7-carboxylate The title compound is prepared from the compound from Example 19c) by reaction with ethyl isocyanate by the process of Example 20a).

Melting point: 182° C.
$R_f$ ($SiO_2$, $CH_2Cl_2$/MeOH/$NH_3$ 9:1:0.2)=0.22
MS(FAB): 549 (M+H)

b) 2-n-Butyl-1-[(2'-ethylaminocarbonylaminosulfonylbiphenyl-4-yl)-methyl]-1H-benzimidazole-7-carboxylic acid This compound results from the compound from 23a) by the process of Example 1b).

Melting point: >220° C.
$R_f$ ($SiO_2$, $CH_2Cl_2$/MeOH/HOAC 9:1:0.2)=0.35
MS (FAB): 535 (M+H)

EXAMPLE 24

2-n-Butyl-1-[(2'-cyclopropylmethylaminocarbonylaminosulfonylbiphenyl-4-yl)methyl]-1H-benzimidazole-7-carboxylic acid a) Methyl 2-n-butyl-1-[(2'-cyclopropylmethylaminocarbonylaminosulfonylbiphenyl-4-yl)methyl]-1H-benzimidazole-7-carboxylate 139 mg (0.29 mmol) of the compound from Example 19c) are stirred at 80° C. for 30 minutes with 35 mg (0.88 mmol)

of powdered NaOH and 67 mg (0.32 mmol) of 2,2,2-trichloro-N-cyclopropylmethylacetamide (prepared from cyclopropylmethylamine and trichloroacetyl chloride) in 2 ml of absolute DMSO under argon. The reaction solution is poured onto ice and acidified with 2N HCl, and the precipitate which deposits is filtered off with suction.

After recrystallization from EA, 69 mg of the title compound result.

Melting point: 158°–161° C.

$R_f$ (SiO$_2$, n-heptane/EA 2:8)=0.23

MS (FAB), 575 (M+H)

b) 2-n-Butyl-1-[(2'-cyclopropylmethylaminocarbonylaminosulfonylbiphenyl-4-yl)methyl]-1H-benzimidazole-7-carboxylic acid The title compound is prepared from the compound of Example 24a) by the process mentioned in Example 1h).

Melting point: 234°–236° C.

$R_f$ (SiO$_2$, CH$_2$Cl$_2$/MeOH/HOAc 9:1:0.2)=0.28

MS (FAB): 561 (M+H)

EXAMPLE 25

2-n-Butyl-3-[(2'-ethoxycarbonylaminosulfonylbiphenyl-4-yl)methyl]-3H-imidazo-[4,5-b]/[5,4-b]-pyridine a) 2-n-Butyl-3-[(2'-N,N-dimethylaminoformylsulfonamidobiphenyl-4-yl)methyl]-3H-imidazo-[4,5b]/[5,4-b]-pyridine The title compound is prepared from the compounds from Examples 4a) and 12d) by the process described in Example 4b). Purification was carried out by chromatography on SiO$_2$ using EA/MeOH 20:1 as the eluent and crystallization from EA/diisopropyl ether.

Melting point: 205°–211° C.

$R_f$ (SiO$_2$, EA/MeOH 20:1)=0.15

MS (FAB): 476 (M+H)

b) 2-n-Butyl-3-[(2'-sulfonamidobiphenyl-4-yl)methyl]-3H-imidazo[4,5-b]/[5,4-b]-pyridine This compound is prepared from the compound from 25a) by the process of Example 19c) and chromatography on SiO$_2$ using EA/MeOH 20:1 as the eluent.

$R_f$ (SiO$_2$, EA/MeOH 20:1)=0.39

MS (FAB): 421 (M+H)

c) 2-n-Butyl-3-[(2'-ethoxycarbonylaminosulfonylbiphenyl-4-yl)methyl]-3H-imidazo-[4,5-b]/[5,4-b]pyridine 1 g (2.38 mmol) of the compound from Example 25b) is heated under reflux for 6 h with 1 g of activated (high vacuum drying at 150° C. for 3 h) molecular sieve 4Å, 0.66 g of K$_2$CO$_3$ and 232 µl of ethyl chloroformate in 25 ml of absolute dimethoxyethane under argon. After cooling, the mixture is treated with 100 ml of 10% strength KH$_2$PO$_4$ solution (pH~4), extracted 3× with EA, and the combined EA extracts are dried over Na$_2$SO$_4$ and concentrated. Chromatography on SiO$_2$ (EA/MeOH 20:1) yields 0.5 g of the title compound.

Melting point: 172° C.

$R_f$ (SiO$_2$, EA/MeOH 20:1)=0.3

MS (FAB): 493 (M+H)

EXAMPLE 26

2-n-Butyl-3-[(2'-isopropylaminocarbonylaminosulfonyl-biphenyl-4-yl)-methyl]-3H-imidazo[4,5-b]/[5,4-b]pyridine The title compound results from 100 mg (0.2 mmol) of the compound from Example 25c) after boiling under reflux for 3 h with 209 µl (2.44 mmol) of isopropylamine in 5 ml of toluene, concentration and chromatography on SiO$_2$ (EA) in a yield of 45 mg.

Melting point: 113°–114° C.

$R_f$ (SiO$_2$, EA/MeOH 20:1)=0.36

MS (FAB): 506 (M+H)

EXAMPLE 27

2-n-Butyl-3-[(2'-allylaminocarbonylaminosulfonylbiphenyl-4-yl)-methyl]-3H-imidazo-[4,5-b]/[5,4-b]pyridine The title compound results from the reaction of the compound from Example 25b) with allyl isocyanate analogously to the process described in Example 20a).

Melting point: 121° C.

$R_f$ (SiO$_2$, EA/MeOH 20:1)=0.26

MS (FAB): 504 (M+H)

EXAMPLE 28

2-n-Butyl-3-[(2'-n-propylaminocarbonylaminosulfonylbiphenyl-4-yl)-methyl]-3H-imidazo-[4,5-b]/[5,4-b]pyridine 150 mg (0.3 mmol) of the compound from Example 25c) are boiled under reflux for 3 h with 295 µl (3.6 mmol) of n-propylamine in 5 ml of toluene. The mixture is concentrated and the residue is chromatographed on SiO$_2$ (EA). 90 mg of the title compound were obtained.

Melting points 137°–138° C.

$R_f$ (SiO$_2$, EA)=0.2

MS (FAB): 506 (M+H)

EXAMPLE 29

2-n-Butyl-3-[(2'-benzyloxycarbonylaminosulfonylbiphenyl-4-yl) methyl]-3H-imidazole-[4,5-b]/[5,4-b]pyridine The title compound is prepared from the compound from Example 25b) and benzyl chloroformate by the process described in Example 25c).

Melting point: 85° C.

$R_f$ (SiO$_2$, EA/MeOH 20:1)=0.29

MS (FAB): 555 (M+H)

EXAMPLE 30

2-Ethyl-7-methyl-3-[(2'-n-propylaminocarbonylaminosulfonylbiphenyl-4-yl) methyl]-imidazo-[4,5-b]-pyridine a) 2-Ethyl-7-methyl-3H-imidazo[4,5-b]pyridine 10 g (65.3 mmol) of 2-amino-4-methyl-3-nitropyridine are hydrogenated in 40 ml of tetrahydrofuran and 40 ml of methanol in the presence of Raney nickel. The catalyst is filtered off, the solvent is removed, the residue is treated with ethanolic HCl solution and the precipitated 2,3-diamino-4-methylpyridine hydrochloride is filtered off with suction. 7 g of this hydrochloride are dissolved in 57 g of polyphosphoric acid (from 28.5 g of $P_2O_5$ and 28.5 g of $H_3PO_4$ (85% strength)) and treated with 1.26 ml of propionic acid, and the solution is stirred at 100° C. for 2 h. After cooling, it is poured into ice-water, rendered alkaline by addition of $Na_2CO_3$ and extracted several times with EA. The combined EA phases are washed with saturated NaCl solution, dried over $Na_2SO_4$ and concentrated and the residue is chromatographed on $SiO_2$ (EA/MeOH 5:1). 4.2 g of the title compound result.

$R_f$ ($SiO_2$, EA/MeOH 5:1)=0.4
MS (DCI): 162 (M+H)

b) 3-[(2'-N,N-dimethylaminoformylsulfonamidobiphenyl-4-yl)methyl]-2-ethyl-7-methyl-imidazo[4,5-b]pyridine 3.1 g (19.26 mmol) of the compound from Example 30a) and 9.15 g (19.26 mmol) of the compound from Example 12d) (75% strength) are stirred over night at room temperature in 200 ml of absolute DMF in the presence of 2.6 g (19.6 mmol) of $K_2CO_3$. The solvent is then removed, the residue is taken up in $CH_2Cl_2$, and the $CH_2Cl_2$ solution is washed with $H_2O$, dried over $Na_2SO_4$ and concentrated. Chromatography on $SiO_2$ (EA/MeOH 20:1) yields 2.8 g of the title compound.

Melting point: 168°–170° C.
$R_f$ (EA/MeOH 20:1)=0.13
MS (FAB): 462 (M+H)

c) 2-Ethyl-7-methyl-3-[(2'-sulfonamidobiphenyl-4-yl)methyl]-imidazo[4,5-b]pyridine 2.8 g (6.06 mmol) of the compound from Example 30b) are converted into the title compound (2.2 g) by the process mentioned in Example 19c).

Melting point: 211°–212° C.
$R_f$ ($SiO_2$, EA/MeOH)=0.35
MS (FAB): 407 (M+H)

d) 2-Ethyl-7-methyl-3-[(2'-n-propylaminocarbonylaminosulfonylbiphenyl-4-yl)methyl]-imidazo[4,5b]pyridine The title compound is prepared from the compound from Example 30c) and n-propyl isocyanate by the process of Example 20a). 43 mg of the desired product result from 70 mg (0.172 mmol) of compound 30c).

Melting point: 215°–220° C.
$R_f$ ($SiO_2$, EA/MeOH 20:1)=0.36
MS (FAB): 492 (M+H)

EXAMPLE 31

2-Ethyl-3-[(2'-ethylaminocarbonylaminosulfonylbiphenyl-4-yl)methyl]-7-methyl-imidazo[4,5-b]pyridine The title compound is prepared from the compound of Example 30c) and ethyl isocyanate by the process of Example 20a).

Melting point: 240°–245° C.
$R_f$ ($SiO_2$, EA)=0.14
MS (FAB): 478 (M+H)

EXAMPLE 32

3-[(2'-allylaminocarbonylaminosulfonylbiphenyl-4-yl)methyl]-2-ethyl-7-methyl-imidazo[4,5-b]pyridine The preparation of the title compound is carried out by reaction of the compound from Example 30c) and allyl isocyanate by the process of Example 20a).

Melting point: 216°–219° C.
$R_f$ ($SiO_2$, EA)=0.13
MS (FAB): 490 (M+H)

EXAMPLE 33

2-Ethyl-3-[(2'-methoxycarbonylaminosulfonylbiphenyl-4-yl)methyl]-7-methyl-imidazo[4,5-b]pyridine 100 mg (0.245 mmol) of the compound from Example 30c) are stirred under reflux for 2 h with 171 mg (1.24 mmol) of $K_2CO_3$, 62 μl (0.62 mmol) of dimethyl dicarbonate and 25 mg of DMAP in 10 ml of diethylene glycol dimethyl ether. The solvent is then distilled off, the residue is treated with an EA/$KH_2PO_4$ solution, and the organic phase is separated and washed 2× with a $KH_2PO_4$ solution. Drying over $Na_2SO_4$, concentration and chromatography on $SiO_2$ (EA) yielded 44 mg of the title compound.

$R_f$ ($SiO_2$, EA): 0.15
MS (FAB): 465 (M+H)

The examples of the formula V shown in the following table were prepared from the building blocks described analogously to the procedures mentioned in Examples 1–33:

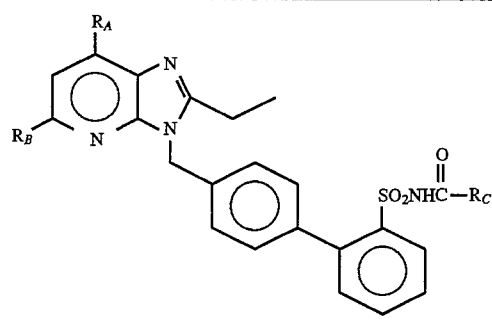

Melting

| Example | $R_A$ | $R_B$ | $R_C$ | Point [°C.] | $R_f$ SiO$_2$ | MS(FAB) [M + H] |
|---|---|---|---|---|---|---|
| 34 | —CH$_3$ | —H |  | | 0.15 (EA) | 447 |
| 35 | —CH$_3$ | —H |  | | 0.17 (EA) | 461 |
| 36 | —CH$_3$ | —H |  | | 0.15 (EA) | 445 |
| 37 | —CH$_3$ | —H |  | | 0.3 (EA/MeOH 20:1) | 509 |
| 38 | —CH$_3$ | —H |  | | 0.2 (EA) | 432 |
| 39 | —CH$_3$ | —H |  | | 0.22 (EA) | 508 |
| 40 | —CH$_3$ | —H |  | | 0.2 (EA) | 500 |
| 41 | —CH$_3$ | —H |  | | 0.28 (EA/MeOH 20:1) | 474 |
| 42 | —CH$_3$ | H |  | | 0.16 (EA) | 472 |
| 43 | —CH$_3$ | H |  | | 0.18 (EA) | 486 |
| 44 | —CH$_3$ | H |  | | 0.3 (EA/MeOH 20:1) | 446 |
| 45 | —CH$_3$ | —CH$_3$ |  | 120 | 0.15 (EA) | 479 |
| 46 | —CH$_3$ | —CH$_3$ |  | | 0.29 (EA) | 555 |
| 47 | —CH$_3$ | —CH$_3$ |  | | 0.3 (EA) | 519 |
| 48 | —CH$_3$ | —CH$_3$ |  | 142 | 0.28 (EA) | 507 |
| 49 | —CH$_3$ | —CH$_3$ |  | 217 | 0.2 (EA) | 488 |
| 50 | —CH$_3$ | —CH$_3$ |  | 205 | 0.2 (EA) | 492 |
| 51 | —CH$_3$ | —CH$_3$ |  | 204 | 0.2 (EA) | 506 |
| 52 | —CH$_3$ | —CH$_3$ |  | 189–191 | 0.3 (EA) | 518 |
| 53 | —CH$_3$ | —CH$_3$ |  | 198 | 0.2 (EA) | 504 |

We claim:
1. A compound of the formula (I)

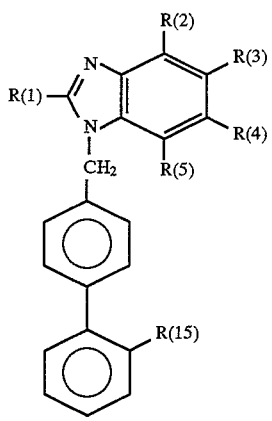

in which the symbols have the following meaning:
R(1) is

1. $(C_1-C_{10})$-alkyl
2. $(C_3-C_{10})$-alkenyl,
3. $(C_3-C_{10})$-alkynyl,
4. $(C_3-C_8)$-cycloalkyl,
5. benzyl, or
6. benzyl which is substituted on the phenyl moiety by 1 or 2 identical or different substituents selected from the group consisting of halogen, $(C_1-C_4)$-alkoxy, and nitro;

R(2), R(3), R(4) and R(5) are identical or different and are:

1. hydrogen,
2. hydroxyl,
3. halogen,
4. a linear or branched $(C_1-C_8)$-alkyl radical, unsubstituted or substituted by one are more identical or different substituents selected from the group consisting of halogen, hydroxyl, $(C_1-C_4)$-alkoxy, $(C_1-C_4)$-alkylthio, and mercapto, or
5. —$CO_2R(6)$;

R(6) is 1. hydrogen,
2. $(C_1-C_8)$-alkyl,
3. $(C_3-C_8)$-cycloalkyl,
4. phenyl,
5. benzyl or
6. $(C_1-C_8)$-alkyl, in which 1 to all of the hydrogen atoms are substituted by fluorine;

R(15) is

1. $SO_2$—NR(18)—CO—O—R(17), or
2. $SO_2$—N(CO—OR(17))$_2$;

R(16) and (R17) are identical or different and are 1. hydrogen,
2. $(C_1-C_6)$-alkyl,
3. $(C_3-C_8)$-cycloalkyl,
4. $(C_6-C_{12})$-aryl,
5. $(C_6-C_{10})$-aryl-$(C_1-C_4)$-alkyl,
6. 2-pyrimidinyl, 1-piperidinyl, or quinuclidinyl,
7. $(C_3-C_6)$-alkenoyl,
8. a radical as defined in 4., 5., 6., 9., 14., 15., 16., 18., 19., or 20. of this subparagraph, substituted by 1 or 2 identical or different substituents selected from the group consisting of hydroxyl, methoxy, nitro, cyano, $CO_2R(6)$, trifluoromethyl, —NR(25)R(26) and

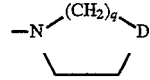

9. $(C_1-C_9)$-heteroaryl-$(C_1-C_3)$-alkyl, where the heteroaryl moiety is partially hydrogenated, completely hydrogenated, or not hydrogenated,
10. $(C_1-C_6)$-alkyl, in which 1 to all of the hydrogen atoms are substituted by fluorine,
11. $(C_2-C_6)$-alkenyl,
12. $(C_3-C_8)$-cycloalkenyl,
13. $(C_3-C_8)$-cycloalkenyl-$(C_1-C_{13})$-alkyl,
14. $(C_3-C_8)$-cycloalkyl-$(C_1-C_4)$-alkyl,
15. $(C_6-C_{10})$-aryl-$(C_3-C_8)$-alkenyl,
16. $(C_1-C_9)$-heteroaryl-$(C_3-C_6)$-alkenyl,
17. $(C_3-C_6)$-alkynyl,
18. $(C_6-C_{10})$-aryl-$(C_3-C_6)$-alkynyl,
19. $(C_1-C_9)$-heteroaryl-$(C_3-C_6)$-alkynyl,
20. a radical of the formula

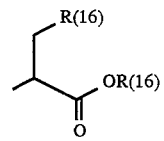

where R(16) cannot have the meaning of 20. of this subparagraph (stereocenters are present either in the R- or in the S-configuration), or 21. R(16)R(17), together with the nitrogen atom bearing them, form a heteroaryl radical which is partially hydrogenated, completely hydrogenated, or not hydrogenated;

R(18) is 1. hydrogen
2. $(C_1-C_6)$-alkyl,
3. $(C_3-C_8)$-cycloalkyl,
4. $(C_6-C_{12})$-aryl-$(C_1-C_6)$-alkyl,
5. phenyl, or
6. $(C_1-C_9)$-heteroaryl;

D is NR(23), O or $CH_2$;
q is zero or 1;
R(23) is hydrogen, halogen, $(C_1-C_4)$-alkyl or $(C_1-C_4)$-alkoxy;
R(25) and R(26) are identical or different and are 1. hydrogen,
2. $(C_1-C_4)$-alkyl
3. phenyl,
4. benzyl or
5. α-methylbenzyl;

or a physiologically tolerable salt thereof.

2. A compound of the formula (I)

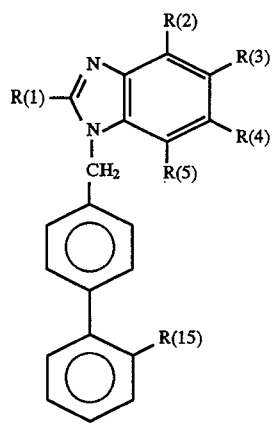

in which the symbols have the following meaning:
R(1) is

1. $(C_1-C_{10})$-alkyl
2. $(C_3-C_{10})$-alkenyl,
3. $(C_3-C_{10})$-alkynyl,
4. $(C_3-C_3)$-cycloalkyl,
5. benzyl, or
6. benzyl which is substituted on the phenyl moiety by 1 or 2 identical or different substituents selected from the group consisting of halogen, $(C_1-C_4)$-alkoxy and nitro;

R(2), R(3), R(4) and R(5) are identical or different and are:

1. hydrogen,
2. hydroxyl,
3. halogen,
4. a linear or branched $(C_1-C_8)$-alkyl radical, unsubstituted or substituted by one or more identical or different substituents selected from the group consisting of halogen, hydroxyl, $(C_1-C_4)$-alkoxy, $(C_1-C_4)$-alkylthio and mercapto, or
5. —$CO_2R(6)$;

R(6) is 1. hydrogen,
2. $(C_1-C_8)$-alkyl,
3. $(C_3-C_8)$-cycloalkyl,
4. phenyl,
5. benzyl, or
6. $(C_1-C_8)$-alkyl, in which 1 to all of the hydrogen atoms are substituted by fluorine;

R(15) is

1. $SO_2$—$NR(18)$—$CO$—$NR(16)R(17)$, or
2. $SO_2$—$NR(18)$—$CO$—$R(17)$;

R(16) and (R17) are identical or different and are 1. hydrogen,
2. $(C_3-C_8)$-cycloalkyl,
3. $(C_6-C_{10})$-aryl-$(C_1-C_4)$-alkyl,
4. 2-pyrimidinyl, 1-piperidinyl, or quinuclidinyl,
5. $(C_3-C_6)$-alkenoyl,
6. a radical as defined in 3., 4., 7., 11., 12., 13., 15., 16., or 17. of this subparagraph, substituted by 1 or 2 identical or different substituents selected from the group consisting of hydroxyl, methoxy, nitro, cyano, $CO_2R(6)$, trifluoromethyl, —$NR(25)R(26)$ and

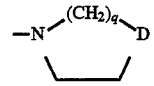

7. $(C_1-C_9)$-heteroaryl-$(C_1-C_3)$-alkyl, where the heteroaryl moiety is partially hydrogenated, completely hydrogenated, or not hydrogenated,
8. $(C_3-C_8)$-cycloalkyl, in which 1 to all of the hydrogen atoms are substituted by fluorine,
9. $(C_3-C_8)$-cycloalkenyl,
10. $(C_3-C_8)$-cycloalkenyl-$(C_1-C_3)$-alkyl,
11. $(C_3-C_8)$-cycloalkyl-$(C_1-C_4)$-alkyl,
12. $(C_6-C_{10})$-aryl-$(C_3-C_8)$-alkenyl,
13. $(C_1-C_9)$-heteroaryl-$(C_3-C_8)$-alkenyl,
14. $(C_3-C_6)$-alkynyl,
15. $(C_6-C_{10})$-aryl-$(C_3-C_8)$-alkynyl,
16. $(C_1-C_9)$-heteroaryl-$(C_3-C_8)$-alkynyl,
17. a radical of the formula

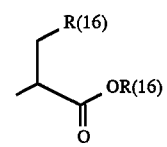

where R(16) cannot have the meaning of 17. of this subparagraph, (stereocenters are present either in the R- or in the S-configuration), or 18. R(16)R(17), together with the nitrogen atom bearing them, form a heteroaryl radical which is partially hydrogenated, completely hydrogenated, or not hydrogenated;

R(18) is 1. hydrogen,
2. $(C_1-C_6)$-alkyl,
3. $(C_3-C_8$-cycloalkyl,
4. $(C_6-C_{12})$-aryl-$(C_1-C_6)$-alkyl,
5. phenyl, or
6. $(C_1-C_9)$-heteroaryl;

D is $NR(23)$, O or $CH_2$;
q is zero or 1;
R(23) is hydrogen, halogen, $(C_1-C_4)$-alkyl or $(C_1-C_4)$-alkoxy;
R(25) and R(26) are identical or different and are 1. hydrogen,
2. $(C_1-C_4)$-alkyl
3. phenyl,
4. benzyl, or
5. α-methylbenzyl;

or a physiologically tolerable salt thereof.

3. A compound of the formula I as claimed in claim 1, in which
R(1) is $(C_1-C_7)$-alkyl, $(C_3-C_7)$-alkenyl or $(C_3-C_7)$-alkynyl;
R(2), R(3) and R(4) are hydrogen;
R(5) is hydrogen, or —$CO_2R(6)$;
R(6) is hydrogen or $(C_1-C_4)$-alkyl; and
R(18) is hydrogen or $(C_1-C_8)$-alkyl.

4. A compound of the formula I as claimed in claim 3, in which

R(16) and R(17) are identical or different and are hydrogen, $(C_1-C_6)$-alkyl, $(C_3-C_8)$-cycloalkyl, $(C_6-C_{12})$-aryl, $(C_6-C_{10})$-aryl-$(C_1-C_4)$-alkyl, $(C_3-C_6)$-alkenoyl, $(C_2-C_6)$-alkenyl, or $(C_3-C8)$-cycloalkyl-$(C_{1-4})$-alkyl.

5. A compound of the formula I as claimed in claim 2, in which

R(1) is $(C_1-C_7)$, $(C_3-C_7)$-alkenyl or $(C_3-C_7)$-alkynyl;

R(2), R(3) and R(4) are hydrogen;

R(5) is hydrogen, or —$CO_2R(6)$;

R(6) is hydrogen or $(C_1-C_4)$-alkyl; and

R(18) is hydrogen or $(C_1-C_6)$-alkyl.

6. A compound of the formula I as claimed in claim 5, in which

R(16) and R(17) are identical or different and are hydrogen, $(C_1-C_6)$-alkyl, $(C_{38})$-cycloalkyl, $(C_8-C_{12})$-aryl, $(C_6-C_{10})$-aryl-$(C_1-C_4)$-alkyl, $(C_3-C_6)$-alkenoyl, $(C_2-C_6)$-alkenyl, or $(C_3-C_8)$-cycloalkyl-$(C_1-C_4)$-alkyl.

7. A pharmaceutical composition comprising a pharmaceutically effective amount of a compound as claimed in claim 1 and a pharmaceutically effective carrier.

8. A method of treating hypertension comprising the step of administering to a host in recognized need thereof an effective amount for said treatment of a compound as claimed in claim 1.

9. A pharmaceutical composition comprising a pharmaceutically effective amount of a compound as claimed in claim 2 and a pharmaceutically effective carrier.

10. A method of treating hypertension comprising the step of administering to a host in recognized need thereof an effective amount for said treatment of a compound as claimed in claim 2.

* * * * *

UNITED STATES PATENT AND TRADEMARK OFFICE
CERTIFICATE OF CORRECTION

PATENT NO. : 5,635,525

DATED : June 03, 1997

INVENTOR(S) : Holger HEITSCH et al.

It is certified that error appears in the above-indentified patent and that said Letters Patent is hereby corrected as shown below:

On the Title page, Item [54], Col. 1, line 3; in the Title, line 3, "PHARMACTICALS" should read --PHARMACEUTICALS--.

Claim 1, column 36, line 20, "$(C_1-C_{13})$" should read --$(C_1-C_3)$--.

Claim 2, column 38, line 18, "$(C_1-C_9$-heteroaryl" should read --$(C_1-C_9)$-heteroaryl--.

Claim 2, column 38, line 44, "$(C_3-C_8$-cycloalkyl" should read --$(C_3-C_8)$-cycloalkyl--.

Claim 4, column 39, line 6, $(C_3-C8)$-cycloalkyl-$(C_1-_4)$-alkyl" should read --$(C_3-C_8)$-cycloalkyl-$(C_1-C_4)$-alkyl--.

Claim 5, column 39, line 9, "$(C_1-C_7)$" should read --$(C_1-C_7)$-alkyl--.

UNITED STATES PATENT AND TRADEMARK OFFICE
CERTIFICATE OF CORRECTION

PATENT NO. : 5,635,525
DATED : June 03, 1997
INVENTOR(S) : Holger HEITSCH et al.

It is certified that error appears in the above-indentified patent and that said Letters Patent is hereby corrected as shown below:

Claim 6, column 39, line 17 "$(C_{38})$-cycloalkyl" should read --$(C_3-C_8)$-cycloalkyl--.

Signed and Sealed this

Twenty-first Day of October 1997

Attest:

*Attesting Officer*

BRUCE LEHMAN

*Commissioner of Patents and Trademarks*